United States Patent
Hartdegen et al.

(10) Patent No.: US 11,284,886 B2
(45) Date of Patent: Mar. 29, 2022

(54) IMPLANT INSERTER

(71) Applicant: Acumed LLC, Hillsboro, OR (US)

(72) Inventors: Vernon R. Hartdegen, Collierville, TN (US); Michael Chad Hollis, Collierville, TN (US); Daniel Sayger, Southaven, MS (US); John Krumme, Woodside, CA (US)

(73) Assignee: Acumed LLC, Hillsboro, OR (US)

( * ) Notice: Subject to any disclaimer, the term of this patent is extended or adjusted under 35 U.S.C. 154(b) by 55 days.

(21) Appl. No.: 16/076,607

(22) PCT Filed: Feb. 8, 2017

(86) PCT No.: PCT/US2017/016931
§ 371 (c)(1),
(2) Date: Aug. 8, 2018

(87) PCT Pub. No.: WO2017/139328
PCT Pub. Date: Aug. 17, 2017

(65) Prior Publication Data
US 2019/0046183 A1 Feb. 14, 2019

Related U.S. Application Data

(60) Provisional application No. 62/292,823, filed on Feb. 8, 2016, provisional application No. 62/355,276, filed on Jun. 27, 2016.

(51) Int. Cl.
*A61B 17/064* (2006.01)
*A61B 17/068* (2006.01)
*A61B 17/10* (2006.01)

(52) U.S. Cl.
CPC ...... *A61B 17/0642* (2013.01); *A61B 17/0644* (2013.01); *A61B 17/0682* (2013.01); *A61B 17/10* (2013.01); *A61B 2017/0645* (2013.01)

(58) Field of Classification Search
CPC ... A61B 17/06; A61B 17/064; A61B 17/0642; A61B 17/0644; A61B 17/0682
See application file for complete search history.

(56) References Cited

U.S. PATENT DOCUMENTS 3,960,147 A 6/1976 Murray
4,411,378 A 10/1983 Warman
(Continued)

FOREIGN PATENT DOCUMENTS

CN 102579116 A 7/2012
CN 104159528 A 11/2014
(Continued)

OTHER PUBLICATIONS

Supplementary Partial European Search Report dated Sep. 13, 2019 for Application No. EP17750664.9, 14 pages.
(Continued)

*Primary Examiner* — Si Ming Ku
(74) *Attorney, Agent, or Firm* — K&L Gates LLP

(57) ABSTRACT

A system for implant delivery includes an implant and an inserter. The implant includes a body that extends between first and second ends. The implant includes retainers extending outwardly from the first and second ends. The retainers are received in corresponding jaws of the inserter. When the implant is connected to the inserter and the inserter is actuated, the implant elastically deforms.

20 Claims, 9 Drawing Sheets

(56) References Cited

U.S. PATENT DOCUMENTS

| | | | |
|---|---|---|---|
| 5,246,443 | A | 9/1993 | Mai |
| 6,059,787 | A | 5/2000 | Allen |
| 9,907,551 | B2 * | 3/2018 | Seavey ............. A61B 17/0642 |
| 2009/0254090 | A1 | 10/2009 | Lizee |
| 2010/0063506 | A1 | 3/2010 | Fox et al. |
| 2012/0024937 | A1 | 2/2012 | Allen |
| 2012/0228355 | A1 | 9/2012 | Combrowski et al. |
| 2013/0030438 | A1 | 1/2013 | Fox |
| 2014/0276830 | A1 | 9/2014 | Cheney |
| 2014/0277516 | A1 | 9/2014 | Miller et al. |
| 2014/0358187 | A1 | 12/2014 | Taber |
| 2015/0133940 | A1 | 5/2015 | Palmer et al. |
| 2016/0030039 | A1 | 2/2016 | Seavey et al. |
| 2016/0199060 | A1 | 7/2016 | Morgan et al. |
| 2016/0338697 | A1 * | 11/2016 | Biedermann ...... A61B 17/0642 |

FOREIGN PATENT DOCUMENTS

| | | | |
|---|---|---|---|
| CN | 104968283 | A | 10/2015 |
| CN | 105188565 | A | 12/2015 |
| DE | 4110123 | A1 | 10/1992 |
| EP | 0253629 | A1 | 1/1988 |
| EP | 2106754 | A1 | 10/2009 |
| EP | 3095393 | A1 | 11/2016 |
| EP | 3273872 | A1 | 1/2018 |
| EP | 3413806 | A1 | 12/2018 |
| JP | 2005532143 | A | 10/2005 |
| JP | 2011-525377 | A | 9/2011 |
| JP | 2016-214869 | A | 12/2016 |
| WO | 9712729 | A2 | 4/1997 |
| WO | 2008129061 | A1 | 10/2008 |
| WO | WO 2009/091770 | A1 | 7/2009 |
| WO | WO 2015/039024 | A1 | 3/2015 |

OTHER PUBLICATIONS

Extended European Search Report dated Oct. 7, 2019 for Application No. EP17750658.1, 10 pages.
International Search Report and Written Opinion dated Apr. 27, 2017 for Application No. PCT/US2017/016914, 6 pages.
International Search Report and Written Opinion dated Jun. 7, 2017 for Application No. PCT/US2017/016931, 11 pages.
Extended European Search Report corresponding to European Application No. 17750664.9; report dated Dec. 20, 2019; (16 pages).
Chinese Office Action corresponding to Chinese Application No. 201780022560.9; report dated Sep. 17, 2020 (17 pages).
Chinese Office Action corresponding to Chinese Application No. 201780022559.6; report dated Oct. 10, 2020; (18 pages).
Australian Office Action corresponding to Australian Application No. 2017217451; report dated Nov. 24, 2020; (7 pages).
Japanese Office Action corresponding to Japanese Application No. 2018-542733; report dated Jan. 5, 2021; (6 pages).
Japanese Office Action corresponding to Japanese Application No. 2018-542734; report dated Feb. 9, 2021; (15 pages).
Chinese Second Office Action corresponding to Chinese Application No. 201780022559.6; report dated Apr. 26, 2021 (18 pages).
Chinese Second Office Action corresponding to Chinese Application No. 201780022559.6; report dated Jul. 20, 2021 (18 pages).
Australian Office Action corresponding to Australian Application No. 2017217392; report dated Jul. 23, 2021; (8 pages).
Israeli Office Action corresponding to Israeli Application No. 261064; report dated Nov. 3, 2021; (3 pages).
Israeli Office Action corresponding to Israeli Application No. 261063; report dated Nov. 3, 2021; (4 pages).

* cited by examiner

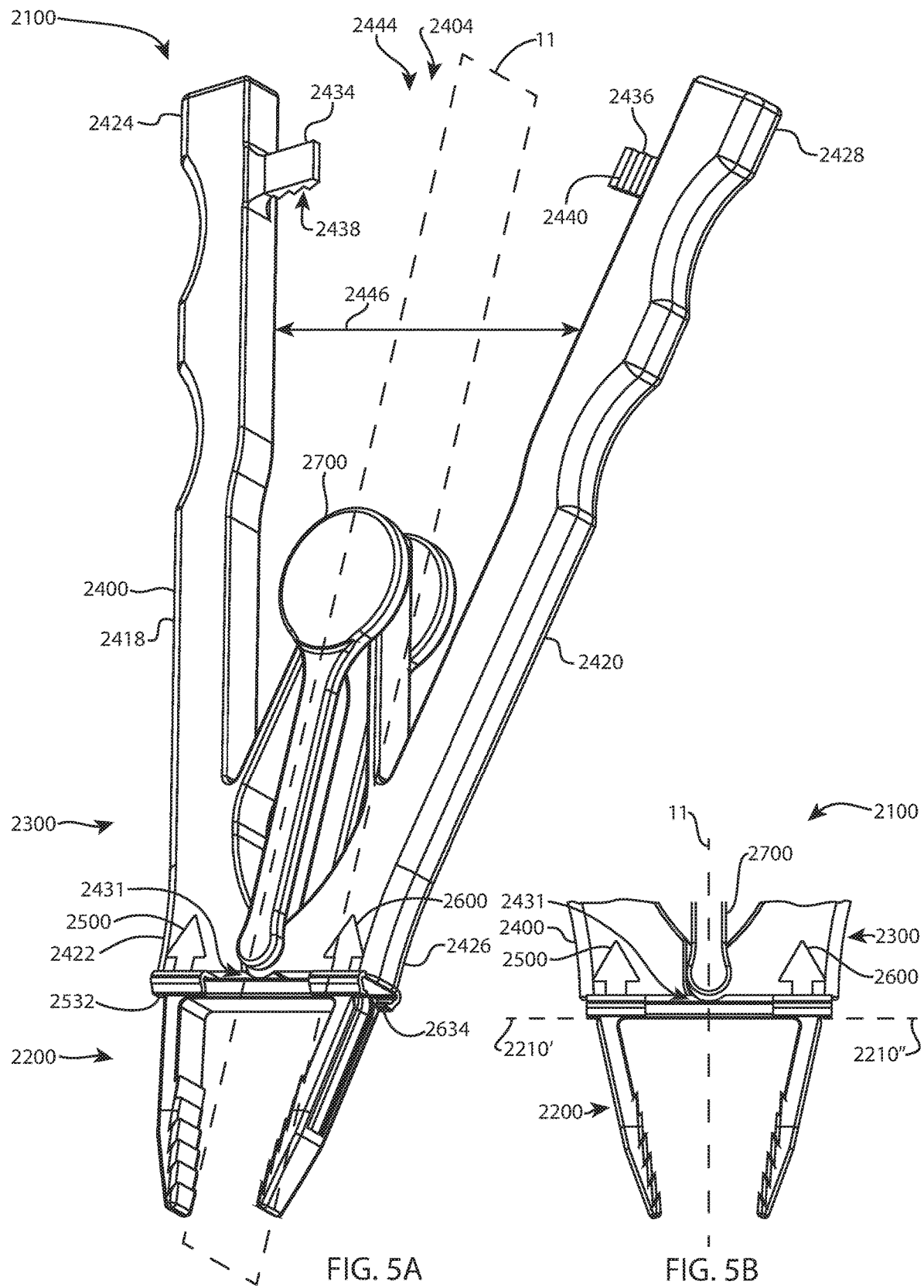

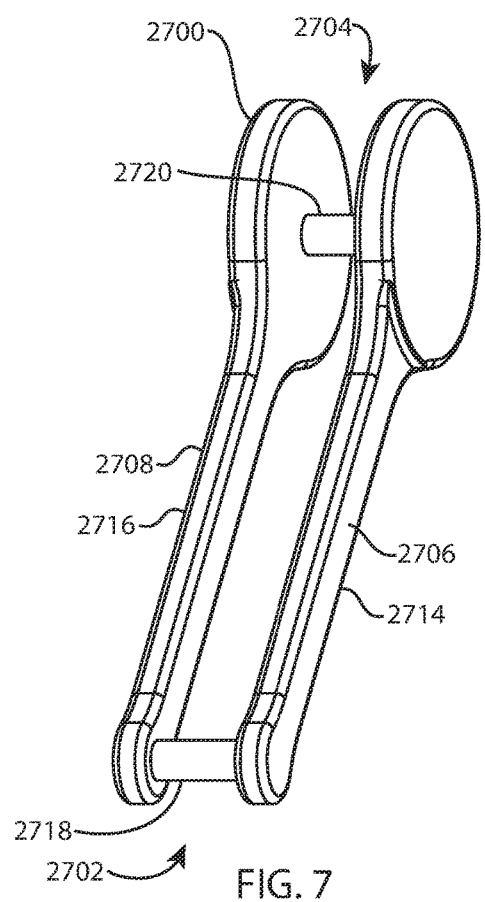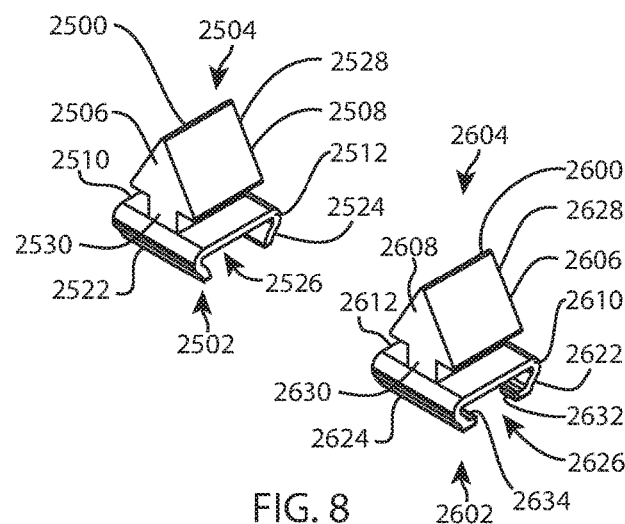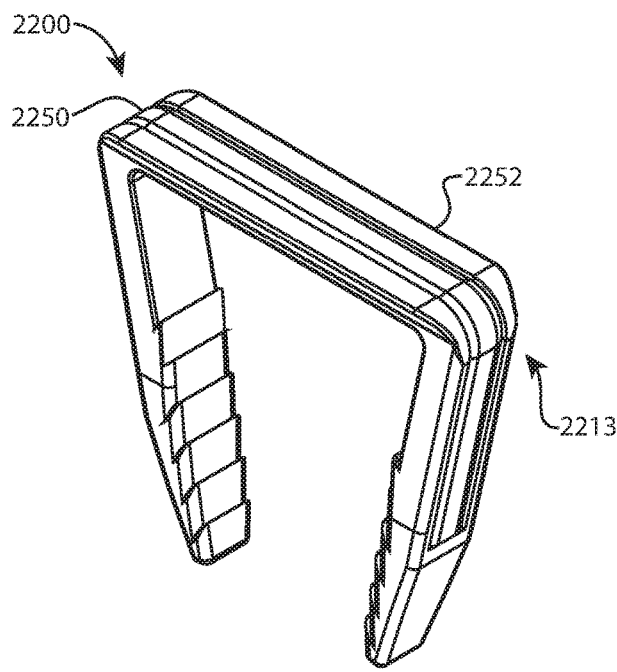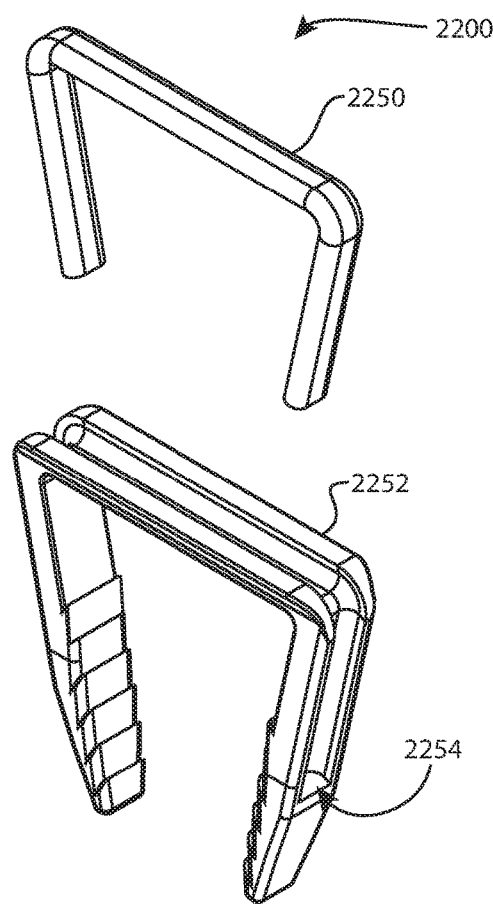
FIG. 7
FIG. 8
FIG. 9A
FIG. 9B

IMPLANT INSERTER

CROSS REFERENCE TO RELATED APPLICATION

The present application claims benefit of International Patent Application (PCT) No. PCT/US2017/016931 filed on Feb. 8, 2017, which claims priority to U.S. Provisional Application Ser. No. 62/292,823 filed on Feb. 8, 2016 and U.S. Provisional Application Ser. No. 62/355,276 filed on Jun. 27, 2016. All of the aforementioned applications are incorporated herein by reference in their entireties.

TECHNICAL FIELD

The present disclosure is made in the context of an inserter for a compression bone staple. However, one of skill in the art will appreciate that the disclosed technology is broadly applicable outside this context to implants that are movable between a free state and an elastically deformed state.

BACKGROUND

Staples of various designs are used for fixation in surgical procedures. In such procedures, two human body parts, e.g. bones, on either side of an interface, are joined together by drilling parallel holes in the body parts on either side of the interface and inserting the legs of a staple into the holes. The legs of the staple are substantially parallel to each other when they are inserted into the holes, but the staple is constructed so that after the staple has been implanted, the ends of the legs converge forcefully towards each other, and thus substantially immobilize the interface. Continuing compression of the body parts has additional benefits, for example continuing compression of bones at the interface promotes bone regrowth. The known surgical staples are composed of a shape memory metal (e.g. a nickel titanium alloy) or an elastic polymeric material, for example polyetherether ketone (PEEK). The known procedures for inserting staples into bones are complicated and expensive.

SUMMARY

The various systems and methods of the present technology have been developed in response to the present state of the art, and in particular, in response to the problems and needs in the art that have not yet been fully solved by currently available systems with implants and inserters.

In an aspect of the technology, a system includes: an implant including a body, a left retainer, and a right retainer, wherein the body extends between a left end and a right end to establish a longitudinal direction of the body, wherein the left retainer protrudes from the left end of the body, wherein the right retainer protrudes from the right end of the body; and an inserter releasably connectable to the implant, the inserter including a left connection, a right connection, and an intermediate connection between the left and right connections; wherein when the inserter is connected to the implant, the left connection engages the left retainer, the right connection engages the right retainer, and the intermediate connection is adjacent to the body; wherein when the inserter is connected to the implant, the system is movable between a free state and an actuated state, wherein in the free state the body is undeformed by the inserter, wherein in the actuated state the body is elastically deformed by pressure from the intermediate connection acting against resistance from the left and right connections.

Various embodiments of this aspect of the technology may include any or all of the following characteristics. The left and right retainers extend along the longitudinal direction of the body. The body extends between a front side and an opposite back side to establish a front to back direction of the body, wherein the left and right retainers extend along the front to back direction. The body extends between a body lower surface and an opposite body upper surface, wherein the left retainer extends between a left lower surface and an opposite left upper surface, wherein the right retainer extends between a right lower surface and an opposite right upper surface, wherein the body upper surface and the left and right lower surfaces are on the same side of the body lower surface. When the inserter is connected to the implant, the body upper surface and the entire inserter are on the same side of the body lower surface. The body lower surface is a bone facing surface. The left connection is a left jaw, wherein the right connection is a right jaw, wherein the intermediate connection is a junction; wherein when the inserter is connected to the implant, the left jaw engages under the left retainer, the right jaw engages under the right retainer, and the junction is adjacent to the body.

In another aspect of the technology, a system includes: an implant including a body, a left retainer, and a right retainer, wherein the body includes a bone contacting surface, wherein the body extends between a left end and a right end to establish a longitudinal direction of the body, wherein the left retainer protrudes from the left end of the body, wherein the right retainer protrudes from the right end of the body; and an inserter releasably connectable to the implant, the inserter including a left connection, a right connection, and an intermediate connection between the left and right connections; wherein when the inserter is connected to the implant, the left connection engages the left retainer, the right connection engages the right retainer, and the intermediate connection is adjacent to the body, wherein the left and right retainers and the entire inserter are all on the same side of the bone contacting surface; wherein when the inserter is connected to the implant, the system is movable between a free state and an actuated state, wherein in the free state the body is undeformed by the inserter, wherein in the actuated state the body is elastically deformed by pressure from the intermediate connection acting against resistance from the left and right connections.

Various embodiments of this aspect of the technology may include any or all of the following characteristics. The left and right retainers extend along the longitudinal direction of the body. The body extends between a front side and an opposite back side to establish a front to back direction of the body, wherein the left and right retainers extend along the front to back direction. The body includes an upper surface opposite the bone contacting surface, wherein the left retainer extends between a left lower surface and an opposite left upper surface, wherein the right retainer extends between a right lower surface and an opposite right upper surface, wherein the upper surface of the body and the left and right lower surfaces are on the same side of the bone contacting surface. The left connection is a left hook, wherein the right connection is a right hook, wherein the intermediate connection is a junction; wherein when the inserter is connected to the implant, the left hook engages under the left retainer, the right hook engages under the right retainer, and the junction is adjacent to the body.

In yet another aspect of the technology, a system includes: a bone staple including a bridge, a left leg, a right leg, a left retainer, and a right retainer, wherein the bridge extends between a left end and a right end to establish a longitudinal direction of the bridge, wherein the left leg includes a left proximal end that is attached to the left end of the bridge, wherein the left leg terminates in a left distal end opposite the bridge, wherein the right leg includes a right proximal end that is attached to the right end of the bridge, wherein the right leg terminates in a right distal end opposite the bridge, wherein the right leg extends beside the left leg, wherein the left and right proximal ends are separated by a first distance, wherein the left retainer is attached to and extends from the left end of the bridge, wherein the right retainer is attached to and extends from the right end of the bridge, wherein the bone staple is movable between a staple free state and an elastically deformed state, wherein when the bone staple is in the staple free state, the staple is undeformed and the left and right distal ends are separated by a second distance which is less than the first distance, wherein when the bone staple is in the elastically deformed state, the left and right distal ends are separated by a third distance which is greater than the second distance; and an inserter releasably connectable to the bone staple, the inserter including a left connector, a right connector, and an intermediate connector, wherein the left connector faces the right connector, wherein the intermediate connector is between the left and right connectors, wherein the inserter is movable between an inserter free state and an actuated state; wherein when the inserter in the inserter free state is connected to the bone staple in the staple free state, the left connector engages the left retainer, the right connector engages the right retainer, and the intermediate connector is adjacent to the bridge, between the left and right ends of the bridge, and opposite the left and right legs; wherein when the inserter in the actuated state is connected to the bone staple in the elastically deformed state, the left connector engages the left retainer, the right connector engages the right retainer, and the intermediate connector presses against the bridge between the left and right ends of the bridge and opposite the left and right legs.

Various embodiments of this aspect of the technology may include any or all of the following characteristics. The left and right retainers extend along the longitudinal direction.

The bridge extends between a front side and an opposite back side to establish a front to back direction of the bridge, wherein the left and right retainers extend along the front to back direction.

The bridge extends between a bridge lower surface and an opposite bridge upper surface, wherein the left retainer extends between a left lower surface and an opposite left upper surface, wherein the right retainer extends between a right lower surface and an opposite right upper surface, wherein the bridge upper surface and the left and right lower surfaces are on the same side of the bridge lower surface. When the inserter is connected to the bone staple, the bridge upper surface and the entire inserter are on the same side of the bridge lower surface. The bridge lower surface is a bone contacting surface. The third distance is equal to the first distance. The third distance is greater than the first distance.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 5A is a perspective view of another system with yet another implant coupled to another inserter; and FIG. 5B is a detail front view of a distal portion of the system of FIG. 5A;

FIG. 7 is a perspective view of a control member of the inserter of FIG. 5A;

FIG. 8 is a perspective view of left and right capture members of the inserter of FIG. 5A; and FIG. 9A is a perspective view of the implant of FIG. 5A; FIG. 9B is an exploded perspective view of the implant of FIG. 5A.

DETAILED DESCRIPTION

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. The sagittal, coronal, and transverse planes are mutually perpendicular. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Figure 1A:
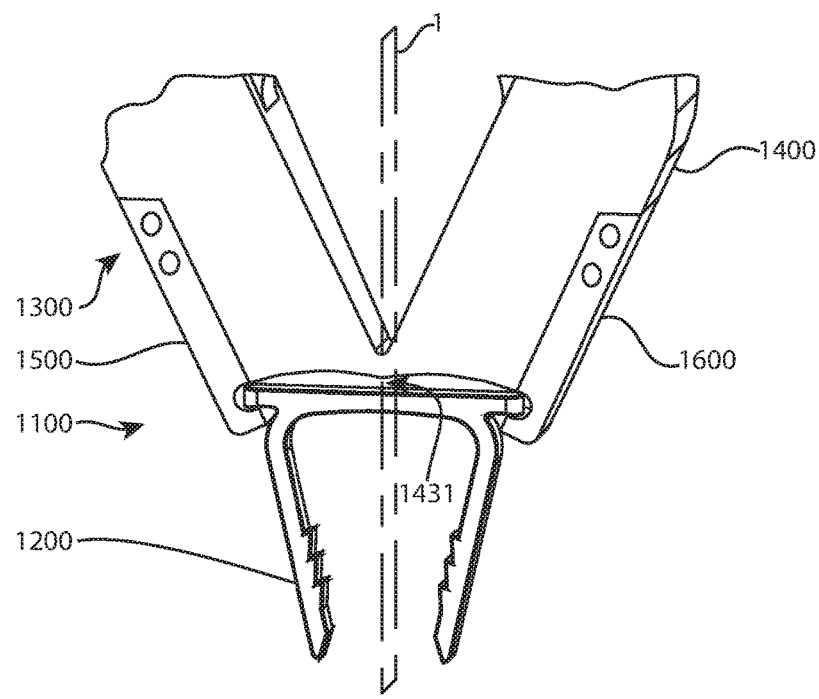
FIG. 1A is a detail perspective view of a distal portion of a system with an implant coupled to an inserter.
Figure 1B:
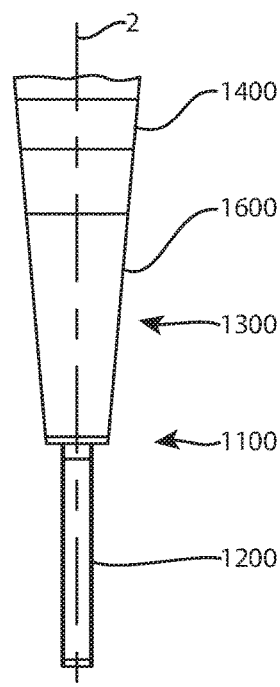
FIG. 1B is a detail side view of a distal portion of the system of FIG. 1A.
Figure 1C:
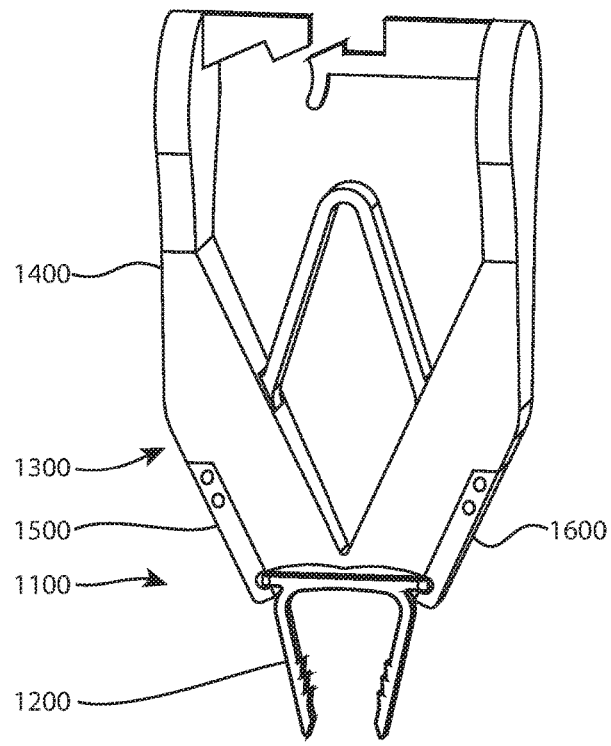
FIG. 1C is a perspective view of the system of FIG. 1A.

Referring to FIGS. 1A-1C, a system 1100 includes an implant 1200 and an inserter 1300. The system 1100 may be referred to as a delivery device and the inserter 1300 may be referred to as a delivery member. The implant 1200 is shown coupled to the inserter 1300, with the implant and inserter in their free states. The illustrated implant 1200 is a compression bone staple.

Figures 2A, 2B:
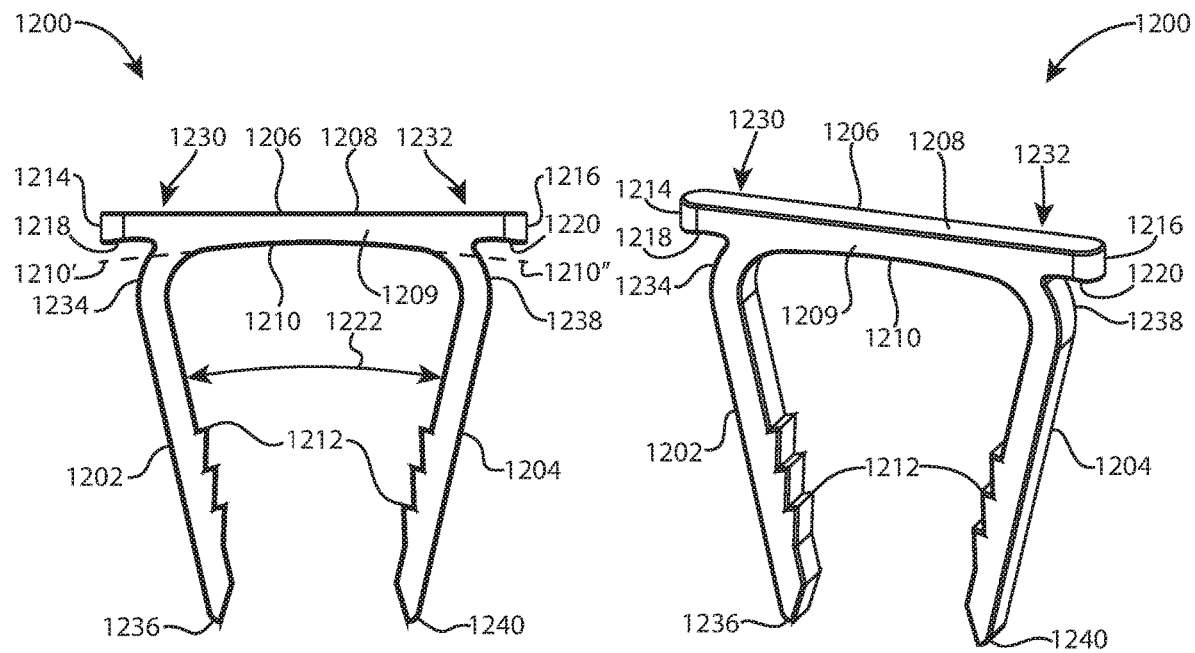
FIG. 2A is a front view of an implant for use in the system of FIG. 1A.
FIG. 2B is a perspective view of the implant of FIG. 2A.

Referring to FIGS. 2A-2B, the implant 1200 includes bone engaging members 1202, 1204 which may be integral to an implant bridge 1206, also referred to as an implant body. The bone engaging members 1202, 1204 may be referred to as legs. The bone engaging member 1202 extends from a left end 1230 of the implant bridge 1206 and the bone engaging member 1204 extends from an opposite right end 1232 of the implant bridge 1206. Bone engaging member 1202 has a proximal end 1234 attached to the left end 1230 of the implant bridge 1206 and an opposite distal end 1236 which is a free end. Bone engaging member 1204 has a proximal end 1238 attached to the right end 1232 of the implant bridge 1206 and an opposite distal end 1240 which is a free end. Implant bridge 1206 has an upper surface 1208, a lower surface 1210, a front surface 1209, and an opposite back surface (not shown). The lower surface 1210 may be referred to as a bone facing surface. Bone engaging member 1202 extends from the lower surface 1210 beside bone engaging member 1204. The bone engaging members 1202, 1204 may have features 1212 that may improve bone purchase or improve pull out strength of the implant 1200 from bone or soft tissue. The features 1212 may be referred to as teeth or serrations. The features 1212 are shown on facing sides of the bone engaging members 1202, 1204 but may be on any or all sides of the bone engaging members. The implant 1200 may have projections or other connecting means 1214, 1216 for connection with a means of insertion, such as inserter 1300. The connecting means 1214, 1216 may be referred to as tabs, ears, protrusions, retainers, wings, or retaining members. The connecting means 1214, 1216 are shown extending sideways outwardly from the ends 1230, 1232 of the bridge 1206, respectively, along a longitudinal direction established by the bridge. However, in other examples, the connecting means may extend outwardly from the ends 1230, 1232 of the bridge 1206, respectively, along a front to back direction. These examples may include four connecting means: left front, left back, right front, and right back. The connecting means 1214, 1216 may have lower surfaces 1218, 1220 respectively that may releasably engage with a means of insertion that may allow the inserter 1300 or other means of insertion to be side loading, top loading or pivotably loaded. For example, the inserter 1300 may be described as side loading or pivotably loading. The lower surfaces 1218, 1220 may be referred to as bone facing surfaces. Referring to FIG. 2A, the lower surfaces 1218, 1220 are proximally spaced apart from, or proximally offset from, from the lower surface 1210. The dashed extension lines 1210', 1210'' in FIG. 2A show the level of the lower surface 1210 versus the lower surfaces 1218, 1220.

The means of insertion may maintain a one piece implant in a first configuration thereby allowing a second implant configuration once the implant is disassembled from the implant. The first configuration may be an elastically deformed state, for example an insertion state. The second configuration may be a free state or an implanted state. The means of insertion may utilize features similar to connecting means 1214 and 1216 in combination with other surfaces such as top surface 1208. This combination of means of insertion may be used to maintain one or more features or arms or projections in a particular configuration. This combination of means of insertion may create a bending modality, such as a three point or four point bend, to maintain a specific implant configuration or combination of configurations. A combination of surfaces and means of insertion, such as connecting means 1214, may be used on the entire implant or portions of an implant to create or maintain a particular configuration of an implant. For example, a tab such as 1214 and top surface, such as 1208 may be used to maintain one side of an implant or one arm of an implant in a particular configuration. When disassembled, that arm may have a configuration that is different from or the same as the configuration of the rest of the implant.

Referring to FIGS. 2A-2B, the implant 1200 is shown uncoupled from the inserter 1300. The implant 1200 is in a free state, or relaxed state, which is the shape of the implant 1200 when no external forces are acting upon the implant 1200, other than gravity; the implant 1200 experiences no elastic or plastic deflection or deformation. In the free state, the bone engaging members 1202, 1204 converge as they extend away from the bridge 1206 so that the distal ends 1236, 1240 are closer together than are the proximal ends 1234, 1238. An angle 1222 is formed between the converging bone engaging members 1202, 1204 in the free state. The angle 1222 opens toward the bridge 1206. The angle 1222 may be referred to as a free state angle.

Figures 3A, 3B:
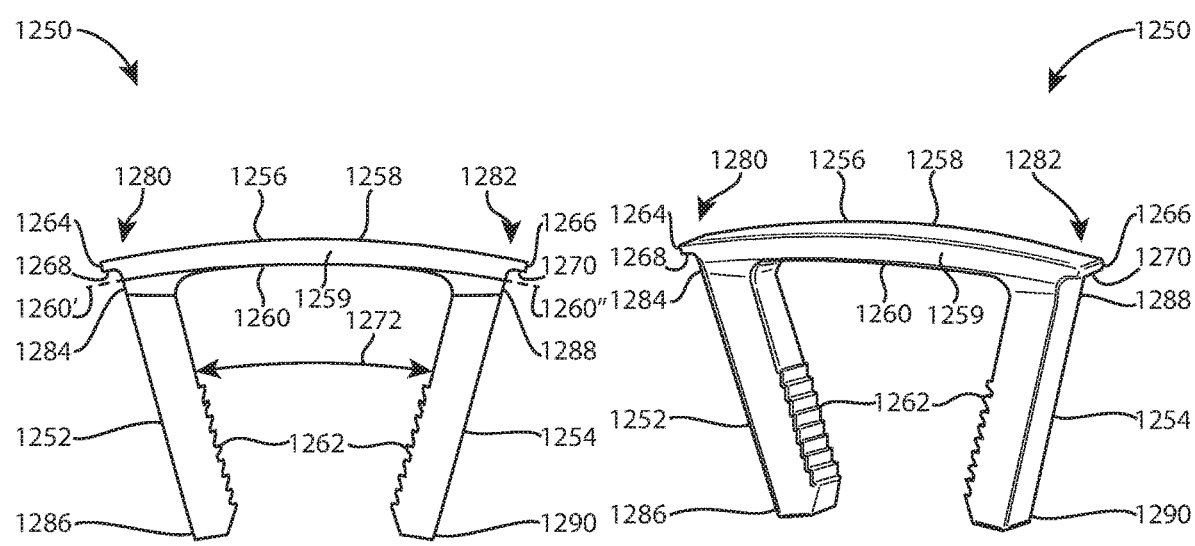
FIG. 3A is a front view of another implant for use in the system of FIG. 1A.
FIG. 3B is a perspective view of the implant of FIG. 2A.
Figure 4A:
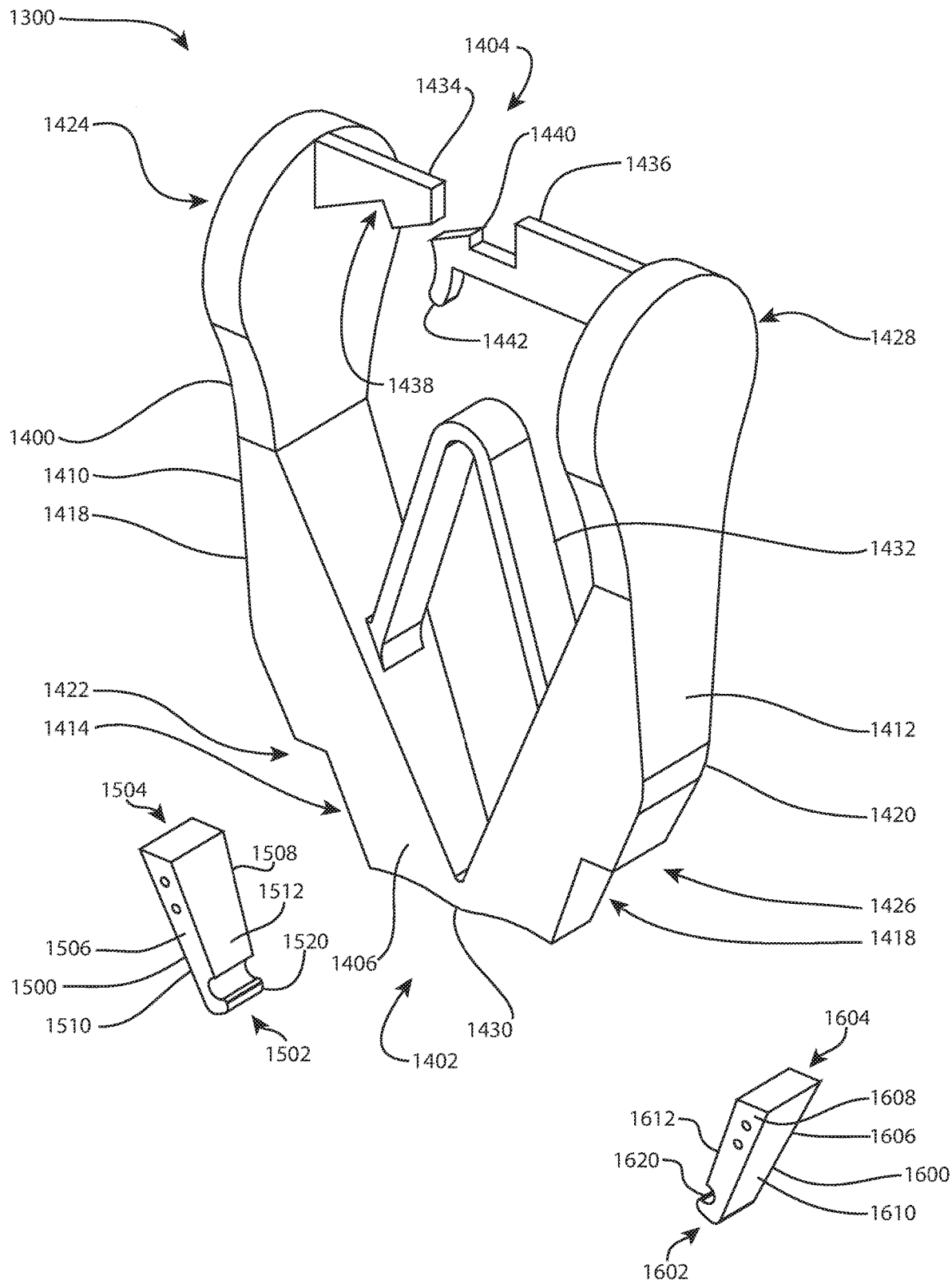
FIG. 4A is an exploded perspective view of the inserter of FIG. 1A.
Figure 4B:
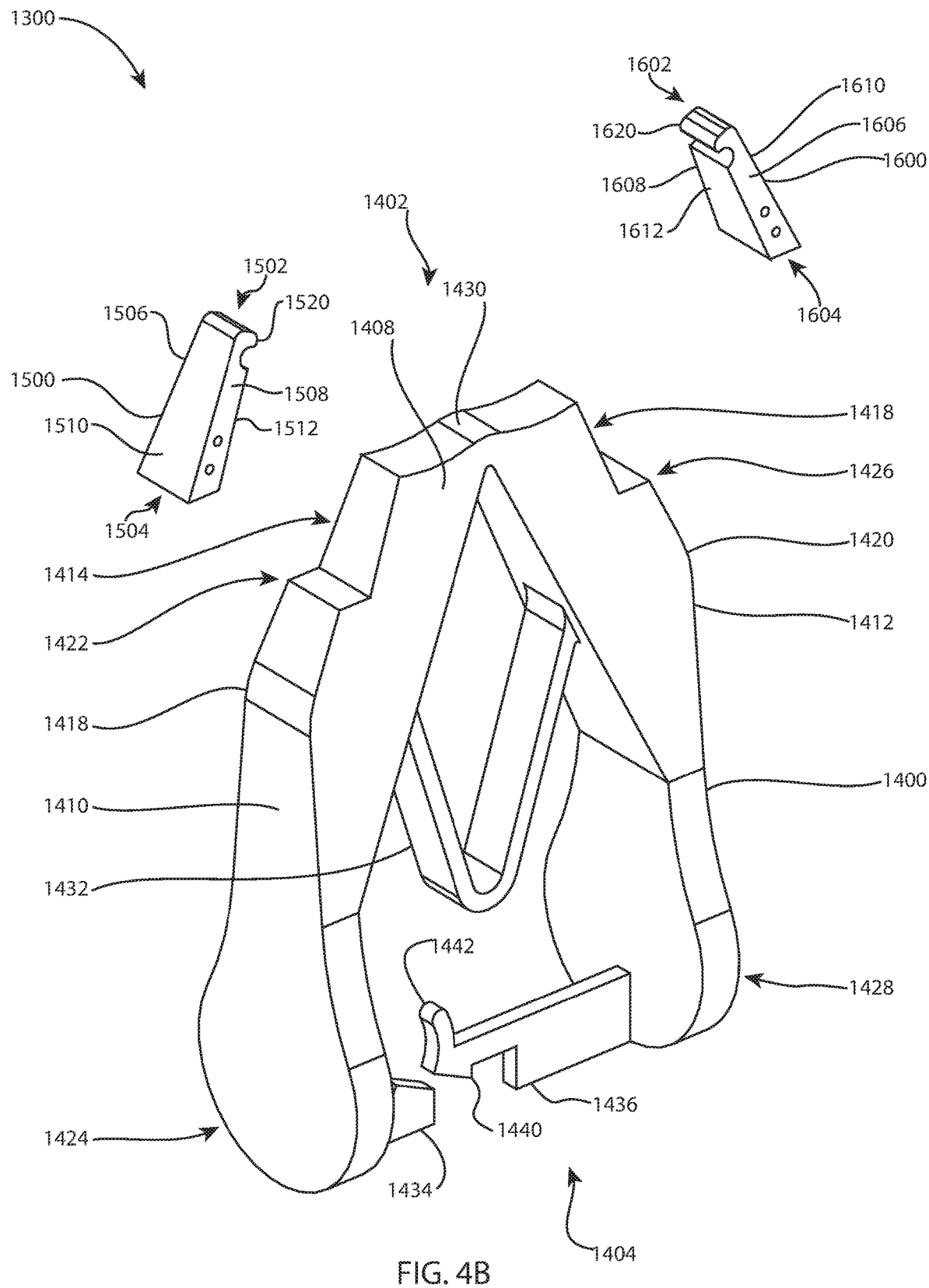
FIG. 4B is another exploded perspective view of the inserter of FIG. 1A from a different direction.

Referring to FIGS. 3A-3B, another implant 1250 may be included in the system 1100 instead of implant 1200. The implant 1250 may be identical to the implant embodiment 2200 described in International Patent Application Serial No. PCT/US2015/039551.

Referring to FIGS. 3A-3B, the implant 1250 includes bone engaging members 1252, 1254 which may be integral to an implant bridge 1256, also referred to as an implant body. The bone engaging members 1252, 1254 may be referred to as legs. The bone engaging member 1252 extends from a left end 1280 of the implant bridge 1256 and the bone engaging member 1254 extends from an opposite right end 1282 of the implant bridge 1256. Bone engaging member 1252 has a proximal end 1284 attached to the left end 1280 of the implant bridge 1256 and an opposite distal end 1286 which is a free end. Bone engaging member 1254 has a proximal end 1288 attached to the right end 1282 of the implant bridge 1256 and an opposite distal end 1290 which is a free end. Implant bridge 1256 has an upper surface 1258, a lower surface 1260, a front surface 1259, and a back surface (not shown). The lower surface 1260 may be referred to as a bone facing surface. Bone engaging member 1252 extends from the lower surface 1260 beside bone engaging member 1254. The bone engaging members 1252, 1254 may have features 1262 that may improve bone purchase or improve pull out strength of the implant 1250 from bone or soft tissue. The features 1262 may be referred to as teeth or serrations. The features 1262 are shown on facing sides of the bone engaging members 1252, 1254 but may be on any or all sides of the bone engaging members. The implant 1250 may have projections or other connecting means 1264, 1266 for connection with a means of insertion, such as inserter 1300. The connecting means 1264, 1266 may be referred to as tabs, ears, protrusions, retainers, wings, or retaining members. The connecting means 1264, 1266 are shown extending sideways outwardly from the ends 1280, 1282 of the bridge 1256, respectively, along a longitudinal direction established by the bridge. However, in other examples, the connecting means may extend outwardly from the ends 1280, 1282 of the bridge 1256, respectively, along a front to back direction. These examples may include four connecting means: left front, left back, right front, and right back. The connecting means 1264, 1266 may have lower surfaces 1268, 1270 respectively that may releasably engage with a means of insertion that may allow the inserter 1300 or other means of insertion to be side loading, top loading or pivotably loaded. For example, the inserter 1300 may be described as side loading or pivotably loading. The lower surfaces 1268, 1270 may be referred to as bone facing surfaces. Referring to FIG. 3A, the lower surfaces 1268, 1270 are proximally spaced apart from, or proximally offset from, from the lower surface 1260. The dashed extension lines 1260', 1260" in FIG. 3A show the level of the lower surface 1260 versus the lower surfaces 1268, 1270.

The means of insertion may maintain a one piece implant in a first configuration thereby allowing a second implant configuration once the implant is disassembled from the implant. The first configuration may be an elastically deformed state, for example an insertion state. The second configuration may be a free state or an implanted state. The means of insertion may utilize features similar to connecting means 1264 and 1266 in combination with other surfaces such as top surface 1258. This combination of means of insertion may be used to maintain one or more features or arms or projections in a particular configuration. This combination of means of insertion may create a bending modality, such as a three point or four point bend, to maintain a specific implant configuration or combination of configurations. A combination of surfaces and means of insertion, such as connecting means 1264, may be used on the entire implant or portions of an implant to create or maintain a particular configuration of an implant. For example, a tab such as 1264 and top surface, such as 1258 may be used to maintain one side of an implant or one arm of an implant in a particular configuration. When disassembled, that arm may have a configuration that is different from or the same as the configuration of the rest of the implant.

Referring to FIGS. 3A-3B, the implant 1250 is shown uncoupled from the inserter 1300. The implant 1250 is in a free state, or relaxed state, which is the shape of the implant 1250 when no external forces are acting upon the implant 1250, other than gravity; the implant 1250 experiences no elastic or plastic deflection or deformation. In the free state, the bone engaging members 1252, 1254 converge as they extend away from the bridge 1256 so that the distal ends 1286, 1290 are closer together than are the proximal ends 1284, 1288. An angle 1272 is formed between the converging bone engaging members 1252, 1254 in the free state. The angle 1272 opens toward the bridge 1256. The angle 1272 may be referred to as a free state angle.

The implants 1200, 1250 may be fabricated from any suitably elastic biocompatible material. The implants 1200, 1250 are preferably made of metal or polymer, preferably nitinol or polyetheretherketone (PEEK).

Referring to FIGS. 1A-1C and 4A-4B, the inserter 1300 includes a body 1400, a first arm 1500, and a second arm 1600. The first and second arms 1500, 1600 are separate component parts in this example, however the first and second arms 1500, 1600 may optionally be integrally formed with the body 1400 as a single part.

The illustrated inserter 1300 has a first plane of symmetry along plane 1 of FIG. 1A and a second plane of symmetry along plane 2 of FIG. 1B, which is shown edge on and is thus represented by a line 2. The first and second planes of symmetry are perpendicular to each other. The first plane of symmetry divides the inserter 1300 into left and right halves. The second plane of symmetry divides the inserter 1300 into front and back halves. The first and second planes of symmetry also apply to the implant 200 and the body 1400. However, in other examples, the inserter 1300 and/or implant 200 may have only one plane of symmetry, or no plane of symmetry so that they are asymmetric.

The body 1400 is an elongated part that extends between a distal end 1402 and an opposite proximal end 1404. The distal end 1402 may be referred to as a working portion and the proximal end 1404 may be referred to as a handle. The body 1400 has a front surface 1406, an opposite back surface 1408, a left side 1410, and an opposite right side 1412. The body 1400 includes a left half 1418 and a right half 1420. The left and right halves 1418, 1420 may be mirror images of each other, except for the clip features discussed below. The left half 1418 has a distal portion 1422 and a proximal portion 1424. The right half 1420 has a distal portion 1426 and a proximal portion 1428.

The left and right halves 1418, 1420 may be joined together by an optional flex bridge 1432, which biases the proximal portions 1424, 1428 away from each other. The flexible bridge 1432 is shown with a bend to enhance flexibility of the flex bridge. The flex bridge 1432 may be replaced by another type of biasing element, such as a spring. The flex bridge 1432 is shown integral with the body 1400, but the flex bridge may be a separate component part, for example a metal ribbon coupled to the left and right halves 1418, 1420.

The distal portions 1422, 1426 may be joined together at a central junction 1430. The junction 1430 may be referred to as an intermediate connection. The body 1400 includes a left arm recess 1414 and a right arm recess 1416. The left arm recess 1414 extends into the left side 1410 at the distal end 1402. The right arm recess 1416 extends into the right side 1412 at the distal end 1402. The right arm recess 1416 is a mirror image of the left arm recess 1414 in this example. When the first and second arms 1500, 1600 are integrally formed with the body 1400, the arm recesses 1414, 1416 are not present.

The proximal portions 1424, 1428 may be enlarged and rounded to form comfortable handles for a user to grasp. The left proximal portion 1424 may optionally include a first clip feature 1434 and the right proximal portion 1428 may optionally include a second clip feature 1436. The first and second clip features 1434, 1436 cooperate to releasably hold the left proximal portion 1424 at a fixed distance from the right proximal portion 1428. The first clip feature 1434 includes a recess 1438 that receives and releasably retains a tooth 1440 included in the second clip feature 1436. Multiple recesses and/or teeth may be included to provide multiple different fixed distances between the proximal portions 1424, 1428. The engagement between the recess 1438 and the tooth 1440 may be released by actuating a lever 1442 or other control feature. The lever 1442 is shown included in the second clip feature 1436 but can instead be included in the first clip feature 1436. The first and second clip features 1434, 1436 may be integral with the body 1400 as shown, or optionally may be separate component parts coupled to the left and right halves 1418, 1420. The clip features 1434, 1436 shown may be replaced with a ratchet mechanism or other releasable retention mechanism.

The first arm 1500 is an elongated part that extends between a distal end 1502 and an opposite proximal end 1504. The first arm 1500 has a front surface 1506, an opposite back surface 1508, an outer side 1510, and an opposite inner side 1512. The distal end 1502 may be referred to as a jaw or a connection. The distal end 1502 terminates in a small hook 1520 that protrudes from the inner side 1512. The hook 1520 may be referred to as a formation, a clip (distinct from the first and second clip features 1434, 1436), a connection, or a capture member.

The second arm 1600 in this example is identical to the first arm 1500. However, to differentiate the two parts, the second arm is given reference number series 1600.

The second arm 1600 is an elongated part that extends between a distal end 1602 and an opposite proximal end 1604. The second arm 1600 has a front surface 1606, an opposite back surface 1608, an outer side 1610, and an opposite inner side 1612. The distal end 1602 may be referred to as a jaw or a connection. The distal end 1602 terminates in a small hook 1620 that protrudes from the inner side 1612. The hook 1620 may be referred to as a formation, a clip (distinct from the first and second clip features 1434, 1436), a connection, or a capture member.

The body 1400 may be fabricated from any suitable material. The body 1400 is preferably made of metal or polymer, preferably stainless steel or polycarbonate. The first and second arms 1500, 1600 may be fabricated from any suitable material. The first and second arms 1500, 1600 are preferably made of metal or polymer, preferably stainless steel or polycarbonate. In one example, the body 1400 is made of a polymer and the first and second arms 1500, 1600 are made of hardened steel. In another example, the body 1400 and the arms 1500, 1600 are integrally formed as a single part made of metal, preferably an elastic metal such as spring steel. In yet another example, the body 1400 and the arms 1500, 1600 are integrally formed as a single part made of polymer.

The first arm 1500 is coupled to the body 1400 so that the distal end 1402 and the distal end 1502 face the same direction, the front surface 1406 and the front surface 1506 face the same direction, the back surface 1408 and the back surface 1508 face the same direction, and the inner side 1512 faces into the left arm recess 1414. The second arm 1600 is coupled to the body 1400 so that the distal end 1402 and the distal end 1602 face the same direction, the front surface 1406 and the back surface 1608 face the same direction, the back surface 1408 and the front surface 1606 face the same direction, and the inner side 1612 faces into the right arm recess 1416. When the first and second arms 1500, 1600 are coupled to the body 1400, the concave sides of the hooks 1520, 1620 face each other. The first and second arms 1500, 1600 may be coupled to the body 1400 by screws, pins, rivets, press fit, dovetail connection, adhesive, over molding, insert molding, or other means. Preferably, the first and second arms 1500, 1600 are rigidly coupled to the body 1400, and are removable for cleaning or replacement. As mentioned previously, the first and second arms 1500, 1600 may optionally be integrally formed with the body 1400 as a single part.

When the inserter 1300 is fully assembled as shown in FIG. 1C, as the proximal portions 1424, 1428 are moved toward each other, the left and right halves 1418, 1420 pivot about the central junction 1430 so that the hooks 1520, 1620 rotate proximally relative to the central junction 1430, the optional flex bridge 1432 deforms so that the proximal bend becomes more pronounced, and, if present, the first and second clip features 1434, 1436 move towards each other so that eventually the tooth 1440 is received in the recess 1438. The flex bridge preferably deforms elastically. When the proximal portions 1424, 1428 are pressed inwardly toward each other against the resistance of the flex bridge 1432, the inserter 1300 is in a compressed state, also referred to as an actuated state. When the tooth 1440 is received in the recess 1438, the inserter 1300 is in a locked state. If there are multiple recesses 1438 and/or teeth 1440, then when the first tooth/recess are engaged, the inserter 1300 is in a first locked state; when the second tooth/recess are engaged, the inserter 1300 is in a second locked state; and so on for third, fourth, or higher locked states. If present, the first and second clip features 1434, 1436 may be disengaged or released by pressing the lever 1442 toward the right proximal portion 1428. As the proximal portions 1424, 1428 are moved away from each other, the left and right halves 1418, 1420 pivot about the central junction 1430 so that the hooks 1520, 1620 rotate distally relative to the central junction 1430, the flex bridge 1432 relaxes so that the proximal bend becomes less pronounced, and, if present, the first and second clip features 1434, 1436 move away from each other. The proximal portions 1424, 1428 may be biased by the flex bridge 1432 to move away from each other automatically as soon as inward pressure on the proximal portions 1424, 1428 is released, or, if present, as soon as the first and second clip features 1434, 1436 are disengaged or released. When the first and second clip features 1434, 1436 are disengaged or released, the inserter 1300 is in an unlocked state. When the flex bridge 1432 has relaxed to its free state, the inserter 1300 is in a free state.

Referring to FIG. 1A-1C, the implant 1200 is shown coupled or connected to the inserter 1300. The implant 1200 and inserter 1300 are each in the free state. The implant 1200 is coupled to the inserter 1300 by engaging the hooks 1520, 1620 of the first and second arms 1500, 1600 under the connecting means 1214, 1216 of the implant 1200, for example by sliding or twisting. The inserter 1300 is secured to, for example, clips over, around, and/or underneath the retaining members of the implant 1200. With the bridge 1206 parallel to the second plane of symmetry as shown in FIGS. 1A-1C, the connecting means 1214, 1216 and the bridge 1206 may slide straight into engagement with the hooks 1520, 1620 from the front or back of the inserter 1300. Alternately, the hooks 1520, 1620 may slide under the connecting means 1214, 1216 along the longitudinal direction established by the bridge. Alternately, with the bridge parallel to the first plane of symmetry, the middle of the bridge 1206 may be placed adjacent to the central junction 1430 and the implant 1200 may be twisted clockwise or counterclockwise relative to the inserter 1300 to rotate the connecting means 1214, 1216 into engagement with the hooks 1520, 1620. When the implant 1200 is coupled to the inserter 1300, the distal portions 1422, 1426 of the body 1400 extend along and above the bridge 1206 of the implant 1200 so that the central junction 1430 is adjacent to a middle portion of the bridge 1206. When the implant 1200 and inserter 1300 are each in the free state, the central junction 1430 is separated from the bridge 1206 by a gap 1431 (FIG. 1A). The proximal portions 1424, 1428 extend away from the bridge 1206 generally opposite the bone engaging members 1202, 1204. The implant 1200 may be pre-loaded on the inserter 1300 in a package, such as a sterile package, with the implant 1200 in the free state. The implant 1200 is also decoupled or disconnected from the inserter 1300 by disengaging the hooks 1520, 1620 of the first and second arms 1500, 1600 from under the connecting means 1214, 1216 of the implant 1200 by sliding or twisting. The connection between the inserter 1300 and the implant 1200 may be ruptured by changing the shape of the inserter 1300 and/or by twisting the inserter 1300 relative to the retaining members. The retaining members remain in place with the implant 1200 after the inserter 1300 has been removed.

Referring to FIGS. 1A, 1C, and 2A, when the implant 1200 is coupled to the inserter 1300, the hooks 1520, 1620 may not extend below the lower surface 1210 of the bridge 1206, due at least in part to the arrangement of the lower surfaces 1218, 1220 of the connecting means 1214, 1216 being proximally offset from the lower surface 1210 of the bridge 1206. Instead, the hooks 1520, 1620 may be even with, or flush with, the lower surface 1210; or proximally spaced apart from, or proximally offset from, the lower surface 1210. More specifically, the distal-most aspect of each hook 1520, 1620 may be at the same level as, or proximal to, the lower surface 1210. This is significant because the lower surface 1210 may contact a bone surface when the implant 1200 is implanted. In examples where the hooks 1520, 1620 are flush with, or proximally offset from, the lower surface, the implant 1200 may be fully seated against the bone surface without interference from the hooks 1520, 1620 against the bone surface. Referring to FIG. 2A, the dashed extension lines 1210', 1210" show the level of the lower surface 1210 when the implant 1200 is in the free state. FIGS. 1A, 1C, and 2A also illustrate that the bridge 1206, connecting means 1214, 1216, and the entire inserter 1300 are located on the proximal side of the lower surface 1210.

Referring to FIGS. 1A-1C, when the implant 1200 is coupled to the inserter 1300, the inserter 1300 may be actuated to urge the implant 1200 into an elastically deformed state. The inserter 1300 may be moved from the free state to the compressed state, or the locked state if the first and second clip features 1434, 1436 are present (or to a first, second, or higher locked state if multiple locked states are enabled by the design of the inserter 1300). As the inserter 1300 moves from the free state to the compressed state or the locked state, the hooks 1520, 1620 rotate proximally relative to the central junction 1430 and the gap 1431 (FIG. 1A) decreases until the central junction 1430 contacts the upper surface 1208 of the bridge 1206 and presses the bridge distally against the resistance of the hooks 1520, 1620 under the connecting means 1214, 1216. In the example, the central junction 1430 contacts and pushes against the middle of the upper surface 1208 to put the bridge into three point bending. However, the central junction 1430 may be designed to contact and push against a different location along the upper surface 1208, or multiple locations. A central junction designed to contact two separate locations along the upper surface 1208 would put the bridge into four point bending, for example. While in the illustrated example, the proximal portions 1424, 1428 are moved toward each other to actuate the inserter 1300, in other examples the proximal portions 1424, 1428 may be moved away from each other, or otherwise moved relative to each other, to actuate the inserter 1300.

Actuating the inserter 1300 from the free state to the compressed state or the locked state puts the implant 1200 into an elastically deformed state in which the distal ends 1236, 1240 of the bone engaging members 1202, 1204 are farther away from each other than they are in the implant free state. The inserter 1300 may urge the implant 1200 into a first elastically deformed state in which the distal ends 1236, 1240 are farther apart than they are in the implant free state, but not as far apart as the proximal ends 1234, 1238, so that the bone engaging members 1202, 1204 still converge slightly; a second elastically deformed state in which the distal ends 1236, 1240 and the proximal ends 1234, 1238 are the same distance apart, so that the bone engaging members 1202, 1204 are parallel, at least to the unaided eye; or a third elastically deformed state in which the distal ends 1236, 1240 are farther apart than are the proximal ends 1234, 1238, so that the bone engaging members 1202, 1204 diverge.

As the inserter 1300 moves from the compressed state or the locked state to the free state, the hooks 1520, 1620 rotate distally relative to the central junction 1430 and the central junction 1430 moves away from the upper surface 1208 of the bridge 1206 to allow the bridge 1206 and the entire implant 1200 to relax toward the implant free state.

The implant 1200 may be decoupled or disconnected from the inserter 1300 when the implant 1200 is in the free state or an elastically deformed state. The inserter 1300 may be decoupled or disconnected from the implant 1200 when the inserter 1300 is in the free state, the unlocked state, the compressed state, or a locked state if the first and second clip features 1434, 1436 are present.

A surgical method for stabilizing first and second bone fragments may include any or all of the following steps in any order: preparing a first hole in the first bone fragment; inserting a temporary fixation pin in the first hole; preparing a second hole in the second bone fragment; determining an implant size corresponding to the first and second holes; selecting the proper size implant 1200; coupling the selected implant 1200 to the inserter 1300, the implant 1200 in the free state; urging the implant 1200 into an elastically deformed state; inserting the bone engaging member 1202 into the first hole and the bone engaging member 1204 into the second hole; seating the lower surface 1210 against a surface of the first or second bone fragment; allowing the implant 1200 to relax toward the implant free state; and decoupling the inserter 1300 from the implant 1200. Allowing the implant 1200 to relax toward the implant free state may comprise releasing inward pressure on the proximal portions 1424, 1428. Optionally, allowing the implant 1200 to relax toward the implant free state may comprise disengaging the first and second clip features 1434, 1436.

Referring to FIGS. 5A-9D, another system 2100 includes an implant 2200 and an inserter 2300. The system 2100 may be referred to as a delivery device and the inserter 2300 may be referred to as a delivery member. In FIGS. 5A-5B, the implant 2200 is shown coupled to the inserter 2300, with the implant 2200 and inserter 2300 in their free states. The illustrated implant 2200 is a compression bone staple.

Referring to FIGS. 5A-5B and 9A-9D, the implant 2200 includes bone engaging members 2202, 2204 which may be integral to an implant bridge 2206, also referred to as an implant body. The bone engaging members 2202, 2204 may be referred to as legs. The bone engaging member 2202 extends from a left end 2230 of the implant bridge 2206 and the bone engaging member 2204 extends from an opposite right end 2232 of the implant bridge 2206. Bone engaging member 2202 has a proximal end 2234 attached to the left end 2230 of the implant bridge 2206 and an opposite distal end 2236 which is a free end. Bone engaging member 2204 has a proximal end 2238 attached to the right end 2232 of the implant bridge 2206 and an opposite distal end 2240 which is a free end. Implant bridge 2206 has an upper surface 2208, a lower surface 2210, a front surface 2209, and a back surface 2211. The lower surface 2210 may be referred to as a bone facing surface. Bone engaging member 2202 extends from the lower surface 2210 beside bone engaging member 2204. The bone engaging members 2202, 2204 may have features 2212 that may improve bone purchase or improve pull out strength of the implant 2200 from bone or soft tissue. The features 2212 may be referred to as teeth or serrations. The features 2212 are shown on facing sides of the bone engaging members 2202, 2204 but may be on any or all sides of the bone engaging members.

Figures 9C, 9D:
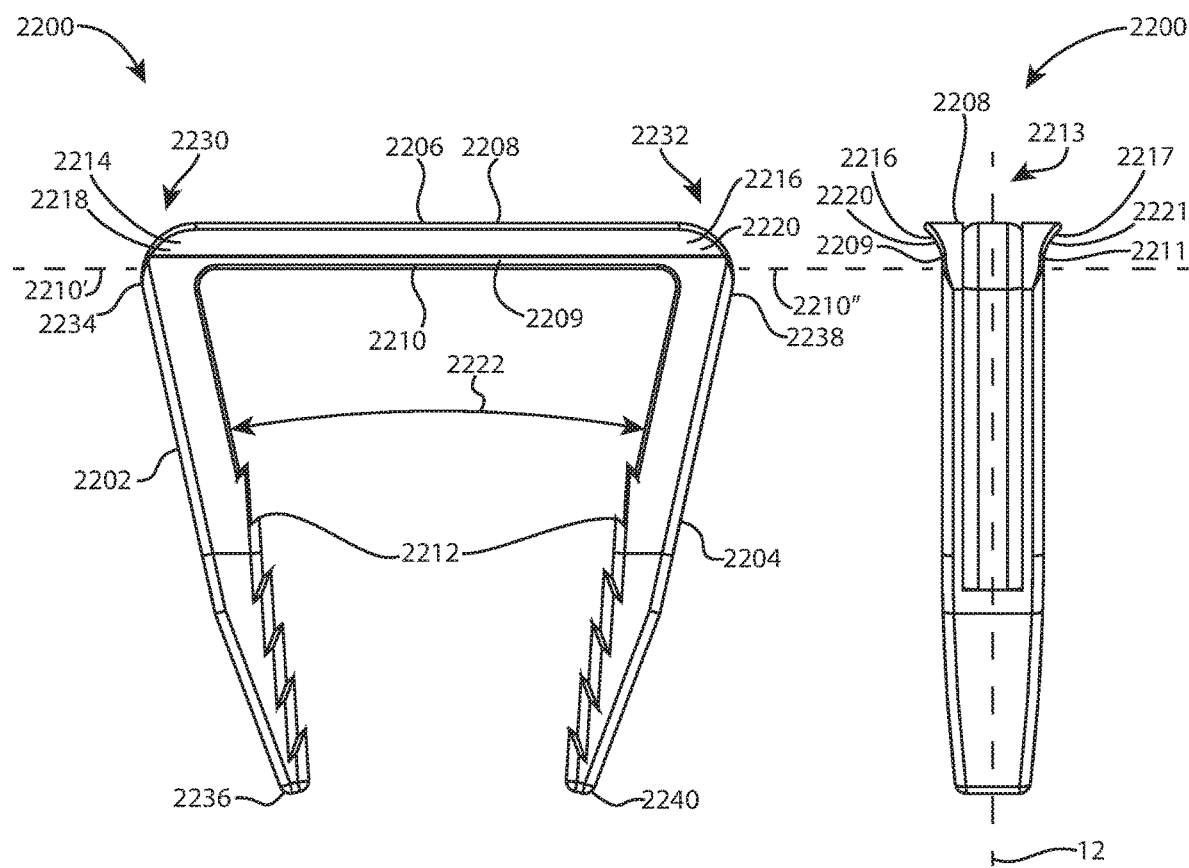
FIG. 9C is a front view of the implant of FIG. 5A.
FIG. 9D is a side view of the implant of FIG. 5A.

The implant 2200 may have projections or other connecting means 2214, 2216 for connection with a means of insertion, such as inserter 2300. The connecting means 2214, 2216 may be referred to as tabs, ears, protrusions, retainers, wings, or retaining members. The connecting means 2214, 2216 are shown extending outwardly from the front surface 2209 from the ends 2230, 2232 of the bridge 2206, respectively, along a front to back direction established between the front surface 2209 and the back surface 2211. This example also includes connecting means 2215, 2217 which are identical to connecting means 2214, 2216, respectively, but which extend outwardly from the back surface 2211 from the ends 2230, 2232 of the bridge 2206, respectively, along the front to back direction. Connecting means 2215 is not visible. The connecting means 2214, 2215, 2216, 2217 have surfaces 2218, 2219, 2220, 2221 respectively. Surface 2219 is not visible. The surfaces 2218, 2219, 2220, 2221 may releasably engage with a means of insertion that may allow the inserter 2300 or other means of insertion to be side loading, top loading, pivotably loaded, or end loading. For example, the inserter 2300 may be described as end loading. The surfaces 2218, 2219, 2220, 2221 may be referred to as bone facing surfaces since they angle outwardly and face distally. Referring to FIGS. 5B and 9D, the surfaces 2218, 2219, 2220, 2221 are proximally spaced apart from, or proximally offset from, from the surface 2210. The dashed extension lines 2210', 2210" in FIGS. 9C-9D show the level of the surface 2210 versus the surfaces 2218, 2220, 2221. In this example, connecting means 2214 and surface 2218 extend across the bridge 2206 toward the right end 2232 to merge with connecting means 2216 and surface 2220. Likewise, connecting means 2217 and surface 2221 extend across the bridge 2206 toward the left end 2230 to merge with connecting means 2215 and surface 2219. Taken together, the connecting means 2214, 2215, 2216, 2217 and surfaces 2218, 2219, 2220, 2221 form a dovetail rail 2213 that extends completely across the bridge 2206 from left to right. However, in other examples, the connecting means 2214, 2215, 2216, 2217 may be discrete features.

Referring to FIGS. 9A-9B, the implant 2200 includes an optional reinforcing member 2250 which may be metal, for example a nickel titanium alloy. When the implant 2200 includes the reinforcing member, the implant may also include a base member 2252, which in this example is the polymer portion of the implant 2200 other than the reinforcing member 2250. The polymer may be PEEK. The base member 2252 may be easily molded with the desired three-dimensional characteristics for the implant 2200. The base member 2252 may include an optional channel 2254 into which the optional reinforcing member 2250 is fitted. The implant 2200 may be referred to as a hybrid implant 2200 because it includes a polymer base member 2252 and a metal reinforcing member 2250. Alternatively, the implant 2200 may lack the reinforcing member 2250 and the channel 2254.

The means of insertion may maintain a one piece implant in a first configuration thereby allowing a second implant configuration once the implant is disassembled from the implant. The first configuration may be an elastically deformed state, for example an insertion state. The second configuration may be a free state or an implanted state. The means of insertion may utilize features similar to connecting means 2214 and 2216 in combination with other surfaces such as top surface 2208. This combination of means of insertion may be used to maintain one or more features or arms or projections in a particular configuration. This combination of means of insertion may create a bending modality, such as a three point or four point bend, to maintain a specific implant configuration or combination of configurations. A combination of surfaces and means of insertion, such as connecting means 2214, may be used on the entire implant or portions of an implant to create or maintain a particular configuration of an implant. For example, a protrusion such as 2214 and top surface, such as 2208 may be used to maintain one side of an implant or one arm of an implant in a particular configuration. When disassembled, that arm may have a configuration that is different from or the same as the configuration of the rest of the implant.

Referring to FIGS. 9A-9D, the implant 2200 is shown uncoupled from the inserter 2300. The implant 2200 is in a free state, or relaxed state, which is the shape of the implant 2200 when no external forces are acting upon the implant 2200, other than gravity; the implant 2200 experiences no elastic or plastic deflection or deformation. In the free state, the bone engaging members 2202, 2204 converge as they extend away from the bridge 2206 so that the distal ends 2236, 2240 are closer together than the proximal ends 2234, 2238. An angle 2222 is formed between the converging bone engaging members 2202, 2204 in the free state. The angle 2222 opens toward the bridge 2206. The angle 2222 may be referred to as a free state angle.

The implant 2200 may be fabricated from any suitably elastic biocompatible material. The implant 2200 is preferably made of metal or polymer, preferably nitinol or polyetheretherketone (PEEK).

Referring to FIGS. 5A-8, the inserter 2300 includes a body 2400, a left capture member 2500, a right capture member 2600, and a control member 2700. The capture members 2500, 2600 are separate component parts in this example, however the capture members 2500, 2600 may optionally be integrally formed with the body 2400 as a single part.

The illustrated inserter 2300 has a first plane of symmetry along plane 11 of FIG. 5A, which is shown edge on in FIG. 5B and is thus represented by a line 11. The inserter 2300 may have a second plane of symmetry along plane 12, which is shown edge on in FIG. 9D and is thus represented by a line 12. The first and second planes of symmetry are perpendicular to each other. The first plane of symmetry divides the inserter 2300 into left and right halves. The second plane of symmetry divides the inserter 2300 into front and back halves. The first and second planes of symmetry also apply to the implant 200, the optional reinforcing member 2250, the base member 2252, the body 2400, and the control member 2700. However, in other examples, the inserter 2300 and/or implant 200 may have only one plane of symmetry, or no plane of symmetry so that they are asymmetric.

Referring to FIGS. 5A-6B, the body 2400 is an elongated part that extends between a distal end 2402 and an opposite proximal end 2404. The distal end 2402 may be referred to as a working portion and the proximal end 2404 may be referred to as a handle. The body 2400 has a front surface 2406, an opposite back surface 2408, a left side 2410, and an opposite right side 2412. The body 2400 includes a left half 2418 and a right half 2420. The left and right halves 2418, 2420 may be mirror images of each other, except for the clip features discussed below. The left half 2418 has a distal portion 2422 and a proximal portion 2424. The right half 2420 has a distal portion 2426 and a proximal portion 2428.

Figure 6A:
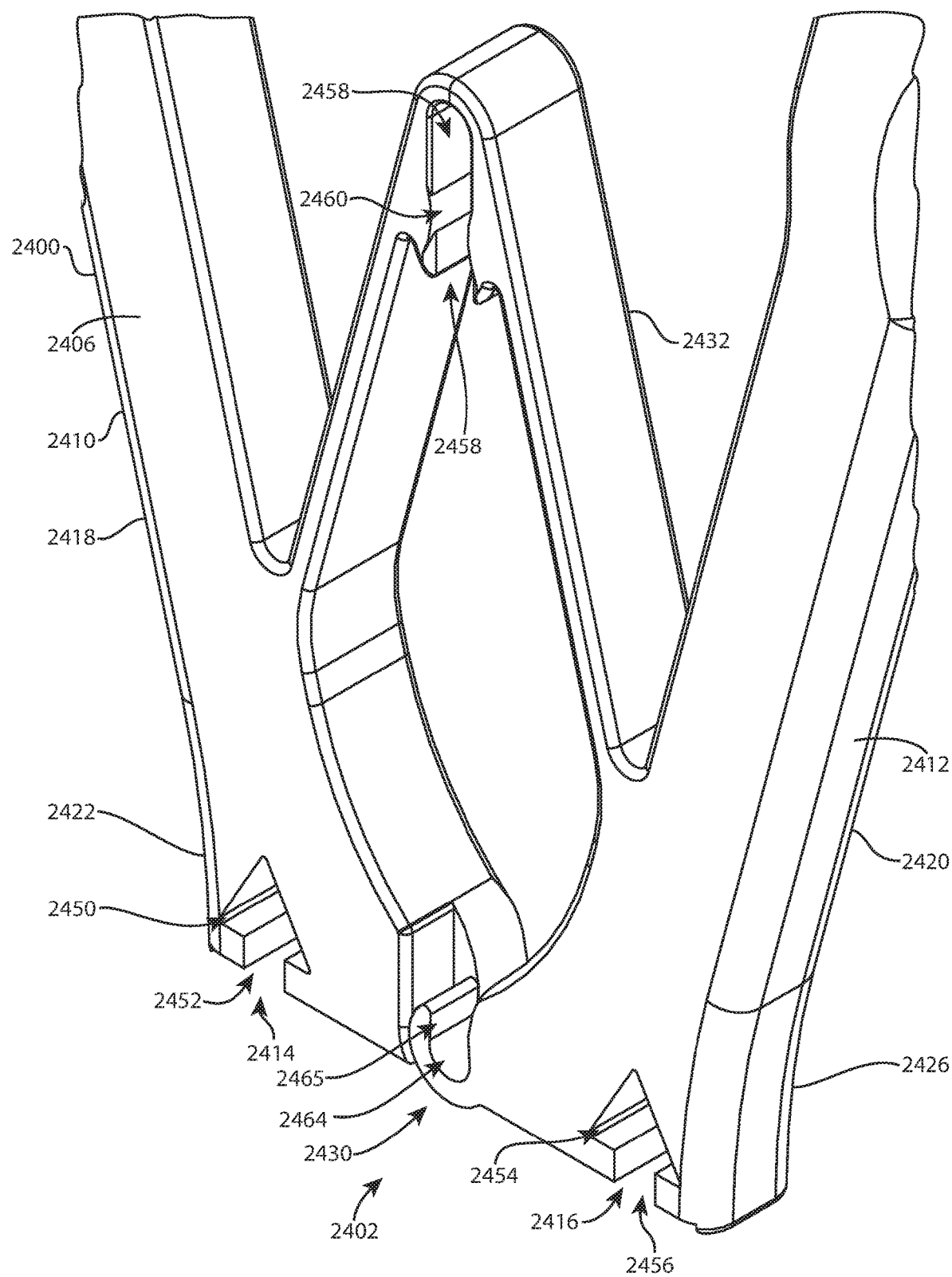
FIG. 6A is a detail perspective view of a distal portion of a body of the inserter of FIG. 5A.
Figure 6B:
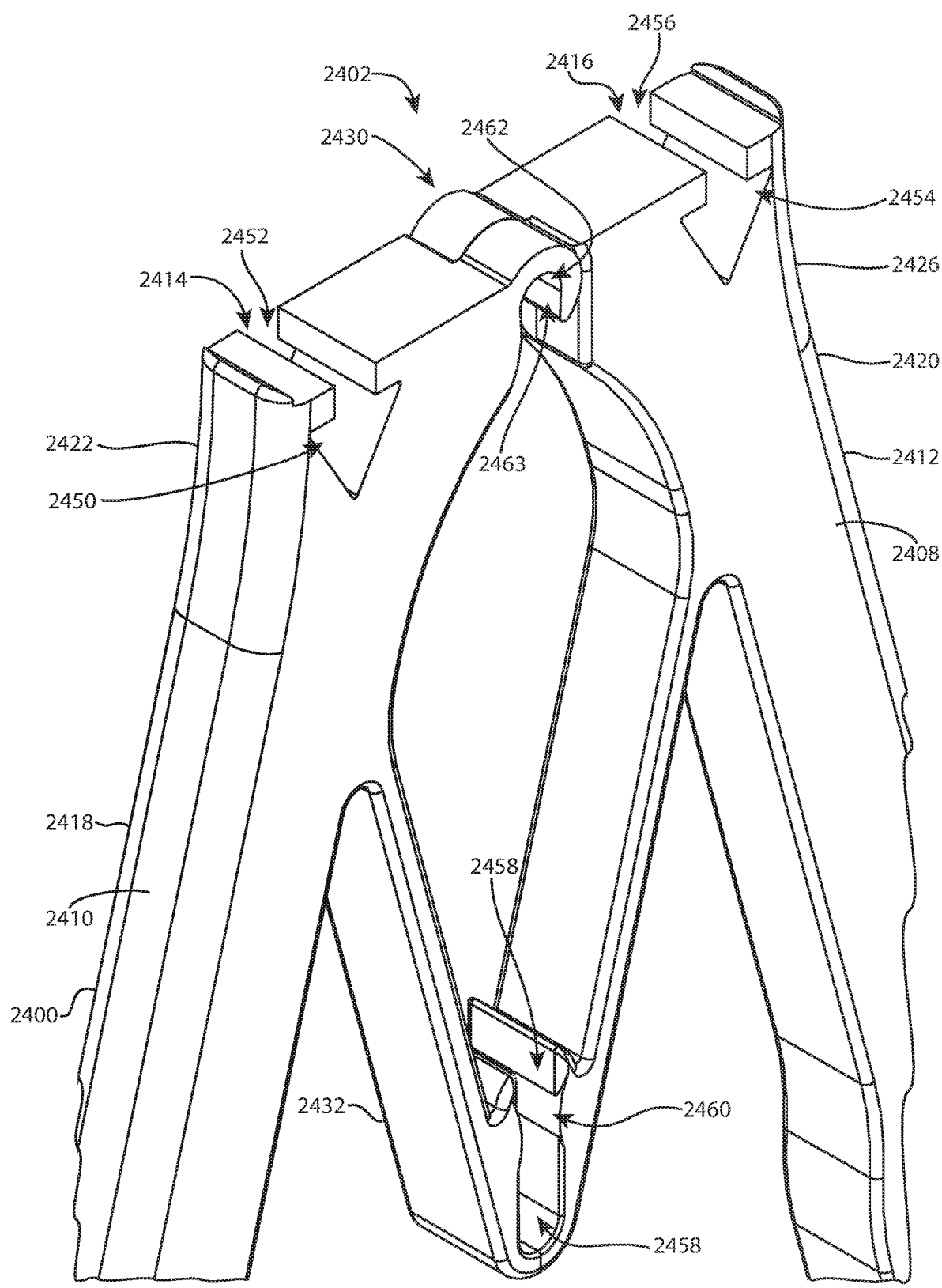
FIG. 6B is another detail perspective view of the distal portion of the body of FIG. 6A from a different direction.

Referring to FIGS. 6A-6B, the left and right halves 2418, 2420 may be joined together by an optional flex bridge 2432, which may bias the proximal portions 2424, 2428 away from each other. The flexible bridge 2432 is shown with a bend which may enhance flexibility of the flex bridge. The flex bridge 2432 may be replaced by another type of biasing element, such as a spring. The flex bridge 2432 is shown integral with the body 2400, but the flex bridge may be a separate component part, for example a metal ribbon coupled to the left and right halves 2418, 2420. Alternatively, the bridge 2432 may have the same flexibility as any other part of the body. The flex bridge 2432 includes a control slot 2458 which may have one or more narrow portions 2460 at intermediate locations along the control slot. One intermediate narrow portion 2460 is shown in this example.

The distal portions 2422, 2426 may meet at a central junction 2430. The junction 2430 may be referred to as an intermediate connection. In this example, the distal portions 2422, 2426 overlap at the central junction 2430. The left distal portion 2422 includes a left control pocket 2462 in the shape of a proximally concave hook at the central junction 2430. The control pocket 2462 may include one or more narrow portions 2463 at locations along the control pocket. One proximal narrow portion 2463 is shown in this example. The right distal portion 2426 includes a right control pocket 2464 in the shape of a proximally concave hook at the central junction 2430. The control pocket 2464 may include one or more narrow portions 2465 at locations along the control pocket. One proximal narrow portion 2465 is shown in this example. The right control pocket 2464 overlaps in front of the left control pocket 2462. This arrangement may be reversed, and may be further modified to include three or more interdigitated control pockets.

The body 2400 includes a left recess 2414 and a right recess 2416. The left recess 2414 extends into the distal end 2402 in the left half 2418. The left recess 2414 includes a proximal wide portion 2450 and a distal narrow portion 2452. The right recess 2416 extends into the distal end 2402 in the right half 2420. The right recess 2416 includes a proximal wide portion 2454 and a distal narrow portion 2456. The left recess 2414 is identical to the right recess 2416 in this example. The recesses 2414, 2416 may be referred to as formations or pockets. The recesses 2414, 2416 are optional, and are present when the capture members 2500, 2600 are separate from the body 2400. When the capture members 2500, 2600 are integrally formed with the body 2400, the recesses 2414, 2416 are not present.

Referring to FIG. 5A, the proximal portions 2424, 2428 may be enlarged and rounded, or otherwise adapted to form comfortable handles for a user to grasp. The left proximal portion 2424 may optionally include a first clip feature 2434 and the right proximal portion 2428 may optionally include a second clip feature 2436. The first and second clip features 2434, 2436 cooperate to releasably hold the left proximal portion 2424 at a fixed distance from the right proximal portion 2428. The first clip feature 2434 includes a groove 2438 that receives and releasably retains a tooth 2440 included in the second clip feature 2436. Multiple grooves and teeth are included to provide a ratchet interconnection that provides multiple different fixed distances between the proximal portions 2424, 2428. The first and second clip features 2434, 2436 may be integral with the body 2400 as shown, or optionally may be separate component parts coupled to the proximal portions 2424, 2428. The clip features 2434, 2436 shown may be replaced with another releasable retention mechanism.

Referring to FIG. 8, the left capture member 2500 has a distal end 2502, an opposite proximal end 2504, a front surface 2506, an opposite back surface 2508, a left side 2510, and an opposite right side 2512. The distal end 2502 may be referred to as a jaw or a connection. The distal end 2502 includes front and back walls 2522, 2524 which define a dovetail groove 2526 between the walls. Taken together, the walls 2522, 2524 and dovetail groove 2526 may be referred to as a formation, a clip (distinct from the first and second clip features 2434, 2436), a connection, or a capture member. The proximal end 2504 includes a locking member 2528 which in this example, when viewed from the front or back, is a proximally pointing triangular feature. A securing member 2530 extends between the locking member 2528 and the distal end 2502. The securing member 2530 is narrower left to right than the locking member 2528, so that bilateral undercuts are formed at the transition between the locking member and the securing member.

The right capture member 2600 in this example is identical to the left capture member 2500. However, to differentiate the two parts, the right capture member is given reference number series 2600.

The right capture member 2600 has a distal end 2602, an opposite proximal end 2604, a front surface 2606, an opposite back surface 2608, a left side 2610, and an opposite right side 2612. The distal end 2602 may be referred to as a jaw or a connection. The distal end 2602 includes front and back walls 2622, 2624 which define a dovetail groove 2626 between the walls. Taken together, the walls 2622, 2624 and dovetail groove 2626 may be referred to as a formation, a clip (distinct from the first and second clip features 2434, 2436), a connection, or a capture member. At the left side 2610, the walls 2622, 2624 include front and back tabs 2632, 2634, respectively, which protrude toward each other, thus narrowing the dovetail groove 2626 at the left side. The tabs are also present on the left capture member 2500 but are not visible in FIG. 8; the front tab 2532 is visible in FIG. 5A. The proximal end 2604 includes a locking member 2628 which in this example, when viewed from the front or back, is a proximally pointing triangular feature. A securing member 2630 extends between the locking member 2628 and the distal end 2602. The securing member 2630 is narrower left to right than the locking member 2628, so that bilateral undercuts are formed at the transition between the locking member and the securing member.

Referring to FIG. 7, the control member 2700 has a distal end 2702, a proximal end 2704, a front surface 2606, and a back surface 2708. A front longitudinal element 2714 extends between the distal end 2702 and the proximal end 2704. A back longitudinal element 2716 extends between the distal end 2702 and the proximal end 2704 and is held spaced apart from the front longitudinal element 2714 by a distal stem 2718 and a proximal stem 2720. The stems 2718, 2720 extend in a front to back direction.

The body 2400, capture members 2500, 2600, and control member 2700 may be fabricated from any suitable material. The body 2400 is preferably made of metal or polymer, preferably stainless steel or polycarbonate. The capture members 2500, 2600 are preferably made of metal or polymer, preferably stainless steel or polycarbonate. The control member 2700 is preferably made of metal or polymer, preferably stainless steel or polycarbonate. In one example, the body 2400 and control member 2700 are made of a polymer and the capture members 2500, 2600 are made of hardened steel. In another example, the body 2400 and the arms 2500, 2600 are integrally formed as a single part made of metal, preferably an elastic metal such as spring steel. In yet another example, the body 2400 and the arms 2500, 2600 are integrally formed as a single part made of polymer.

Referring to FIG. 5A, when the inserter 2300 is operatively assembled, the left capture member 2500 is coupled to the body 2400 so that the distal ends 2402, 2502 face the same direction, the front surfaces 2406, 2506 face the same direction, and the left sides 2410, 2510 face the same direction. The wide portion 2450 of the left recess 2414 receives the locking member 2528 and the narrow portion 2452 receives at least a portion of the securing member 2530. The right capture member 2600 is coupled to the body 2400 so that the distal ends 2402, 2602 face the same direction, the front surface 2406 and the back surface 2608 face the same direction, and the right side 2412 and the left side 2610 face the same direction. The wide portion 2454 of the right recess 2416 receives the locking member 2628 and the narrow portion 2456 receives at least a portion of the securing member 2630 The recesses 2414, 2416 engage the bilateral undercuts so that tension may be applied to the capture members 2500, 2600 by the inserter 2300. The recesses 2414, 2416 may receive the securing members 2530, 2630 and locking members 2528, 2628 with a close fit or an interference fit, and may even be formed around the securing members 2530, 2630 and locking members 2528, 2628 (or vice versa) in a molding operation. When the capture members 2500, 2600 are coupled to the body 2400, the dovetail grooves 2526, 2626 are aligned with each other. The capture members 2500, 2600 may be coupled to the body 2400 by screws, pins, rivets, press fit, dovetail connection, adhesive, over molding, insert molding, or other means. Preferably, the capture members 2500, 2600 are rigidly coupled to the body 2400, and are removable for cleaning or replacement. As mentioned previously, the capture members 2500, 2600 may optionally be integrally formed with the body 2400 as a single part. The control member 2700 is coupled to the body 2400 by inserting the proximal stem 2720 in the control slot 2458, preferably proximally past the narrow portion(s) 2460, so that the front longitudinal element 2714 is adjacent to the front surface 2406 and the back longitudinal element 2716 is adjacent to the back surface 2408. Alternatively, the back longitudinal element 2716 may be adjacent to the front surface 2406 and the front longitudinal element 2714 may be adjacent to the back surface 2408. The distal stem 2718 may then be inserted into the control pockets 2462, 2464 by moving the control member 2700 distally, preferably so that the distal stem 2718 moves past the narrow portions 2463, 2465, preferably until the distal stem 2718 is fully distally seated in the control pockets 2462, 2464. When the distal stem 2718 is in the control pockets 2462, 2464, the proximal stem 2720 may be distally positioned in the control slot 2458 distal to at least a proximal one of the narrow portion(s) 2460, or distally spaced outside the control slot 2458.

When the inserter 2300 is fully assembled as shown in FIG. 5A, with the distal stem 2718 in the control pockets 2462, 2464, as the proximal portions 2424, 2428 are moved toward each other, the gap 2444 becomes smaller, the left and right halves 2418, 2420 pivot about the central junction 2430 so that the capture members 2500, 2600 rotate proximally relative to the central junction 2430, the optional flex bridge 2432 may deform so that the proximal bend becomes more pronounced, and, if present, the first and second clip features 2434, 2436 move towards each other so that eventually the tooth 2440 is received in the groove 2438. The flex bridge preferably deforms elastically. When the proximal portions 2424, 2428 are pressed inwardly toward each other against the resistance of the flex bridge 2432, the inserter 2300 is in a compressed state, also referred to as an actuated state. When the tooth 2440 is received in the groove 2438, the inserter 2300 is in a locked state. Since there are multiple grooves 2438 and teeth 2440 in this example, then when the first tooth/recess are engaged, the inserter 2300 is in a first locked state; when the second tooth/recess are engaged, the inserter 2300 is in a second locked state; and so on for third, fourth, or higher locked states. When the distal stem 2718 is in the control pockets 2462, 2464, the control member 2700 is in a first control position. When the inserter 2300 is connected to the implant 2200 and the control member 2700 is in the first control position, the inserter 2300 is captive to the implant 2200; the inserter 2300 cannot be disconnected from the implant 2200. When the inserter 2300 is not connected to the implant 2200 and the control member 2700 is in the first control position, the inserter cannot be connected to the implant 2200.

If present, the first and second clip features 2434, 2436 may be disengaged or released by the user after the implant 2200 is implanted. With the control member 2700 in the first control position, as the proximal portions 2424, 2428 are moved away from each other, the left and right halves 2418, 2420 pivot about the central junction 2430 so that the capture members 2500, 2600 rotate distally relative to the central junction 2430, the flex bridge 2432 relaxes so that the proximal bend becomes less pronounced, and, if present, the first and second clip features 2434, 2436 move away from each other. The proximal portions 2424, 2428 may be biased by the flex bridge 2432 to move away from each other automatically as soon as inward pressure on the proximal portions 2424, 2428 is released, or, if present, as soon as the first and second clip features 2434, 2436 are disengaged or released. When the first and second clip features 2434, 2436 are disengaged or released, the inserter 2300 is in an unlocked state. When the flex bridge 2432 has relaxed to its free state, the inserter 2300 is in a free state. In the free state, the proximal portions 2424, 2428 are separated by a gap 2444 having a free state dimension 2446.

With the inserter 2300 in the free state, the control member 2700 may be moved proximally to move the proximal stem 2720 into the control slot 2458, preferably past at least a distal one of the narrow portion(s) 2460, preferably until the proximal stem 2720 is fully proximally seated in the control slot 2458; and to move the distal stem 2718 out of the control pockets 2462, 2464, preferably proximally past the narrow portions 2463, 2465. When the distal stem 2718 is out of the control pockets 2462, 2464, the control member 2700 is in a second control position in which the inserter 2300 is connectable to, and disconnectable from, the implant 2200. The inserter 2300 may now be actuated to connect or disconnect the inserter 2300 and the implant 2200.

As the proximal portions 2424, 2428 are moved toward each other, the gap 2444 becomes smaller, the left and right halves 2418, 2420 pivot about the proximal stem 2720 so that the capture members 2500, 2600 rotate outwardly left and right, respectively, relative to the proximal stem 2720, and, if present, the first and second clip features 2434, 2436 move towards each other so that eventually the tooth 2440 is received in the groove 2438.

As the proximal portions 2424, 2428 are moved away from other, the gap 2444 becomes larger, the left and right halves 2418, 2420 pivot about the proximal stem 2720 so that the capture members 2500, 2600 rotate inwardly from left and right, respectively, relative to the proximal stem 2720, and, if present, the first and second clip features 2434, 2436 move away from each other.

Referring to FIGS. 5A-5B, the implant 2200 is shown coupled or connected to the inserter 2300. The implant 2200 and inserter 2300 are each in the free state. With the control member 2700 in the second control position, the implant 2200 may be coupled to the inserter 2300 by actuating the inserter 2300, engaging the dovetail grooves 2526, 2626 of the capture members 2500, 2600 to the connecting means 2214, 2215, 2216, 2217 of the implant 2200, for example by sliding, and spreading apart the proximal portions 2424, 2428 of the inserter 2300. The inserter 2300 is secured to, for example, clips over, around, and/or underneath the connecting means of the implant 2200. With the bridge 2206 parallel to the second plane of symmetry as shown in FIGS. 5A-5B, the dovetail grooves 2526, 2626 may slide straight into engagement with the connecting means 2214, 2215, 2216, 2217 along the longitudinal direction established by the bridge 2206. In the example shown, the dovetail grooves 2526, 2626 slide onto the dovetail rail 2213. When the implant 2200 is coupled to the inserter 2300, the distal portions 2422, 2426 of the body 2400 extend along and above the bridge 2206 of the implant 2200 so that the central junction 2430 is adjacent to a middle portion of the bridge 2206. When the implant 2200 and inserter 2300 are each in the free state, the central junction 2430 may contact the bridge 2206, or the central junction 142 may optionally be separated from the bridge by a gap 2431. The proximal portions 2424, 2428 extend away from the bridge 2206 generally opposite the bone engaging members 2202, 2204. The implant 2200 may be pre-loaded on the inserter 2300 in a package, such as a sterile package, with the implant 2200 in the free state.

With the control member 2700 in the second control position, the implant 2200 may be decoupled or disconnected from the inserter 2300 by actuating the inserter 2300, disengaging the dovetail grooves 2526, 2626 from the connecting means 2214, 2215, 2216, 2217 by sliding the dovetail grooves 2526, 2626 outwardly left and right. The connection between the inserter 2300 and the implant 2200 may be ruptured by changing the shape of the inserter 2300.

Referring to FIGS. 5A-5B, when the implant 2200 is coupled to the inserter 2300, the walls 2522, 2524, 2622, 2624 may not extend below the lower surface 2210 of the bridge 2206, due at least in part to the arrangement of the surfaces 2218, 2219, 2220, 2221 of the connecting means 2214, 2215, 2216, 2217 being proximally offset from the lower surface 2210 of the bridge 2206. Instead, the walls 2522, 2524, 2622, 2624 may be even with, or flush with, the lower surface 2210; or proximally spaced apart from, or proximally offset from, the lower surface 2210. More specifically, the distal-most aspect of each wall 2522, 2524, 2622, 2624 may be at the same level as, or proximal to, the lower surface 2210. This is significant because the lower surface 2210 may contact a bone surface when the implant 2200 is implanted. In examples where the walls 2522, 2524, 2622, 2624 are flush with, or proximally offset from, the lower surface 2210, the implant 2200 may be fully seated against the bone surface without interference from the walls 2522, 2524, 2622, 2624 against the bone surface. Referring to FIG. 9C, the dashed extension lines 2210', 2210" show the level of the lower surface 2210 when the implant 2200 is in the free state. FIG. 5B illustrates that the bridge 2206, connecting means 2214, 2215, 2216, 2217, and the entire inserter 2300 are located on the proximal side of the lower surface 2210.

Referring to FIGS. 5A-5B, when the implant 2200 is coupled to the inserter 2300, the inserter 2300 may be actuated to urge the implant 2200 into an elastically deformed state. The inserter 2300 may be moved from the free state to the compressed state, or to a first, second, or higher locked state if the first and second clip features 2434, 2436 are present. With the control member 2700 in the first control position, as the inserter 2300 moves from the free state to the compressed state or the locked state, the capture members 2500, 2600 rotate proximally relative to the central junction 2430 and the gap 2431 decreases until the central junction 2430 contacts the upper surface 2208 of the bridge 2206 and presses the bridge distally against the resistance of the dovetail grooves 2526, 2626 engaged with the connecting means 2214, 2215, 2216, 2217. The control member 2700 may press distally against the central junction 2430 as the inserter 2300 is actuated. In the example, the central junction 2430 contacts and pushes against the middle of the upper surface 2208 to put the bridge into three point bending. However, the central junction 2430 may be designed to contact and push against a different location along the upper surface 2208, or multiple locations. A central junction designed to contact two separate locations along the upper surface 2208 would put the bridge into four point bending, for example. While in the illustrated example, the proximal portions 2424, 2428 are moved toward each other to actuate the inserter 2300, in other examples the proximal portions 2424, 2428 may be moved away from each other, or otherwise moved relative to each other, to actuate the inserter 2300.

Actuating the inserter 2300 from the free state to the compressed state or the locked state puts the implant 2200 into an elastically deformed state in which the distal ends 2236, 2240 of the bone engaging members 2202, 2204 are farther away from each other than they are in the implant free state. The inserter 2300 may urge the implant 2200 into a first elastically deformed state in which the distal ends 2236, 2240 are farther apart than they are in the implant free state, but not as far apart as the proximal ends 2234, 2238, so that the bone engaging members 2202, 2204 still converge slightly; a second elastically deformed state in which the distal ends 2236, 2240 and the proximal ends 2234, 2238 are the same distance apart, so that the bone engaging members 2202, 2204 are parallel, at least to the unaided eye; or a third elastically deformed state in which the distal ends 2236, 2240 are farther apart than are the proximal ends 2234, 2238, so that the bone engaging members 2202, 2204 diverge.

As the inserter 2300 moves from the compressed state or the locked state to the free state, the capture members 2500, 2600 rotate distally relative to the central junction 2430 and the central junction 2430 moves away from the upper surface 2208 of the bridge 2206 to allow the bridge 2206 and the entire implant 2200 to relax toward the implant free state.

In this example, the implant 2200 may be decoupled or disconnected from the inserter 2300 when the implant 2200 is in the free state or an elastically deformed state. The inserter 2300 may be decoupled or disconnected from the implant 2200 when the inserter 2300 has been prepared for implant disconnection by moving the control member 2700 to the second control position.

A surgical method for stabilizing first and second bone fragments may include any or all of the following steps in any order: preparing a first hole in the first bone fragment; inserting a temporary fixation pin in the first hole; preparing a second hole in the second bone fragment; determining an implant size corresponding to the first and second holes; selecting the proper size implant 2200; coupling the selected implant 2200 to the inserter 2300, the implant 2200 in the free state; urging the implant 2200 into an elastically deformed state; inserting the bone engaging member 2202 into the first hole and the bone engaging member 2204 into the second hole; seating the lower surface 2210 against a surface of the first or second bone fragment; allowing the implant 2200 to relax toward the implant free state; and decoupling the inserter 2300 from the implant 2200. Allowing the implant 2200 to relax toward the implant free state may comprise releasing inward pressure on the proximal portions 2424, 2428. Optionally, allowing the implant 2200 to relax toward the implant free state may comprise disengaging the first and second clip features 2434, 2436.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A system comprising:
an implant comprising a body, a right leg, a left leg, a left retainer, and a right retainer, wherein the body extends between a left end and a right end to establish a longitudinal direction of the body, wherein the left retainer protrudes from the left end of the body, wherein the right retainer protrudes from the right end of the body; and
an inserter releasably connectable to the implant, the inserter comprising
a body having a left half and a right half,
a biasing element that joins the left half to the right half, and
a left connection, a right connection, and an intermediate connection between the left and right connections;
wherein when the inserter is connected to the implant in an actuated state such that the right and left legs of the implant are parallel, the left connection engages the left retainer, the right connection engages the right retainer, and the intermediate connection is adjacent to and protrudes towards the body of the implant such that the intermediate connection contacts a middle portion of the body of the implant at a contact point while a gap is present, the gap enclosed by the body of the implant and a surface of the right half of the body of the inserter between the contact point and the right connection; and
wherein when the inserter is connected to the implant, the system is movable between a free state and the actuated state, wherein in the free state the body is undeformed by the inserter, wherein in the actuated state the body is elastically deformed by pressure from the intermediate connection acting against resistance from the left and right connections.

2. The system of claim 1, wherein the left and right retainers extend along the longitudinal direction of the body.

3. The system of claim 1, wherein the body extends between a front side and an opposite back side to establish a front to back direction of the body, wherein the left and right retainers extend along the front to back direction.

4. The system of claim 1, wherein the body extends between a body lower surface and an opposite body upper surface, wherein the left retainer extends between a left lower surface and an opposite left upper surface, wherein the right retainer extends between a right lower surface and an opposite right upper surface, wherein the body upper surface and the left and right lower surfaces are on the same side of the body lower surface.

5. The system of claim 4, wherein when the inserter is connected to the implant, the body upper surface and the entire inserter are on the same side of the body lower surface.

6. The system of claim 5, wherein the body lower surface is a bone facing surface.

7. The system of claim 1, wherein the left connection is a left jaw, wherein the right connection is a right jaw, wherein the intermediate connection is a junction;

wherein when the inserter is connected to the implant, the left jaw engages under the left retainer, the right jaw engages under the right retainer, and the junction is adjacent to the body.

8. A system comprising:
an implant comprising a body, a right leg, a left leg, a left retainer, and a right retainer, wherein the body comprises a bone contacting surface, wherein the body extends between a left end and a right end to establish a longitudinal direction of the body, wherein the left retainer protrudes from the left end of the body, wherein the right retainer protrudes from the right end of the body; and
an inserter releasably connectable to the implant, the inserter comprising
a body having a left half and a right half,
a biasing element that joins the left half to the right half, and
a left connection, a right connection, and an intermediate connection between the left and right connections;
wherein when the inserter is connected to the implant in an actuated state such that the right and left legs of the implant are parallel, the left connection engages the left retainer, the right connection engages the right retainer, and the intermediate connection is adjacent to and protrudes towards the body of the implant such that the intermediate connection contacts a middle portion of the body of the implant at a contact point while a gap is present, the gap enclosed by the body of the implant and a surface of the right half of the body of the inserter between the contact point and the right connection, wherein the left and right retainers and the entire inserter are all on the same side of the bone contacting surface; and
wherein when the inserter is connected to the implant, the system is movable between a free state and the actuated state, wherein in the free state the body is undeformed by the inserter, wherein in the actuated state the body is elastically deformed by pressure from the intermediate connection acting against resistance from the left and right connections.

9. The system of claim 8, wherein the left and right retainers extend along the longitudinal direction of the body.

10. The system of claim 8, wherein the body extends between a front side and an opposite back side to establish a front to back direction of the body, wherein the left and right retainers extend along the front to back direction.

11. The system of claim 8, wherein the body comprises an upper surface opposite the bone contacting surface, wherein the left retainer extends between a left lower surface and an opposite left upper surface, wherein the right retainer extends between a right lower surface and an opposite right upper surface, wherein the upper surface of the body and the left and right lower surfaces are on the same side of the bone contacting surface.

12. The system of claim 8, wherein the left connection is a left hook, wherein the right connection is a right hook, wherein the intermediate connection is a junction;
wherein when the inserter is connected to the implant, the left hook engages under the left retainer, the right hook engages under the right retainer, and the junction is adjacent to the body.

13. A system comprising:
a bone staple comprising a bridge, a left leg, a right leg, a left retainer, and a right retainer, wherein the bridge extends between a left end and a right end to establish a longitudinal direction of the bridge, wherein the left leg comprises a left proximal end that is attached to the left end of the bridge, wherein the left leg terminates in a left distal end opposite the bridge, wherein the right leg comprises a right proximal end that is attached to the right end of the bridge, wherein the right leg terminates in a right distal end opposite the bridge, wherein the right leg extends beside the left leg, wherein the left and right proximal ends are separated by a first distance, wherein the left retainer is attached to and extends from the left end of the bridge, wherein the right retainer is attached to and extends from the right end of the bridge, wherein the bone staple is movable between a staple free state and an elastically deformed state, wherein when the bone staple is in the staple free state, the staple is undeformed and the left and right distal ends are separated by a second distance which is less than the first distance, wherein when the bone staple is in the elastically deformed state, the left and right distal ends are separated by a third distance which is greater than the second distance; and
an inserter releasably connectable to the bone staple, the inserter comprising
a body having a left half and a right half,
a biasing element that joins the left half to the right half, and
a left connector, a right connector, and an intermediate connector, wherein the left connector faces the right connector, wherein the intermediate connector is between the left and right connectors, wherein the inserter is movable between an inserter free state and an actuated state;
wherein when the inserter in the inserter free state is connected to the bone staple in the staple free state, the left connector engages the left retainer, the right connector engages the right retainer, and the intermediate connector is adjacent to and protrudes towards the bridge, between the left and right ends of the bridge, and opposite the left and right legs; and
wherein when the inserter in the actuated state is connected to the bone staple in the elastically deformed state such that the right and left legs of the implant are parallel, the left connector engages the left retainer, the right connector engages the right retainer, and the intermediate connector presses against a middle portion of the bridge at a contact point, between the left and right ends of the bridge and opposite the left and right legs, while a gap is present, the gap enclosed by the body of the implant and a surface of the right half of the body of the inserter between the contact point and the right connector.

14. The system of claim 13, wherein the left and right retainers extend along the longitudinal direction.

15. The system of claim 13, wherein the bridge extends between a front side and an opposite back side to establish a front to back direction of the bridge, wherein the left and right retainers extend along the front to back direction.

16. The system of claim 13, wherein the bridge extends between a bridge lower surface and an opposite bridge upper surface, wherein the left retainer extends between a left lower surface and an opposite left upper surface, wherein the right retainer extends between a right lower surface and an opposite right upper surface, wherein the bridge upper surface and the left and right lower surfaces are on the same side of the bridge lower surface.

17. The system of claim 16, wherein when the inserter is connected to the bone staple, the bridge upper surface and the entire inserter are on the same side of the bridge lower surface.

18. The system of claim 17, wherein the bridge lower surface is a bone contacting surface.

19. The system of claim 13, wherein the third distance is equal to the first distance.

20. The system of claim 13, wherein the third distance is greater than the first distance.

* * * * *